United States Patent
Schmitz et al.

(10) Patent No.: US 9,476,816 B2
(45) Date of Patent: Oct. 25, 2016

(54) PROBE TIP HEATING ASSEMBLY

(71) Applicant: Hysitron, Inc., Eden Prairie, MA (US)

(72) Inventors: Roger William Schmitz, Hutchinson, MN (US); Yunje Oh, Medina, MN (US)

(73) Assignee: Hysitron, Inc., Eden Prairie, MN (US)

( * ) Notice: Subject to any disclaimer, the term of this patent is extended or adjusted under 35 U.S.C. 154(b) by 0 days.

(21) Appl. No.: 14/358,065

(22) PCT Filed: Nov. 14, 2012

(86) PCT No.: PCT/US2012/065009
§ 371 (c)(1),
(2) Date: May 14, 2014

(87) PCT Pub. No.: WO2013/074623
PCT Pub. Date: May 23, 2013

(65) Prior Publication Data
US 2014/0326707 A1    Nov. 6, 2014

Related U.S. Application Data

(60) Provisional application No. 61/559,699, filed on Nov. 14, 2011.

(51) Int. Cl.
*G01N 3/40* (2006.01)
*H05B 3/03* (2006.01)
(Continued)

(52) U.S. Cl.
CPC ........ *G01N 3/40* (2013.01); *G01N 3/42* (2013.01); *G01Q 30/02* (2013.01); *G01Q 30/10* (2013.01);
(Continued)

(58) Field of Classification Search
CPC .......... B82Y 35/00; G01N 3/40; G01N 3/42; G01N 2203/0226; G01N 2203/0282; G01Q 30/02; G01Q 30/10; G01Q 60/366; H05B 3/03
USPC ................................................ 219/201, 221
See application file for complete search history.

(56) References Cited

U.S. PATENT DOCUMENTS 3,896,314 A    7/1975    Nukuri et al.
4,491,788 A    1/1985    Zandonatti
(Continued)

FOREIGN PATENT DOCUMENTS

EP    0855452 A1    7/1998
GB    2116459 A     9/1993
(Continued)

OTHER PUBLICATIONS

"U.S. Appl. No. 13/510,825, Non Final Office Action mailed Jun. 3, 2014", 28 pgs.
(Continued)

*Primary Examiner* — David Angwin
*Assistant Examiner* — Amit K Singh
(74) *Attorney, Agent, or Firm* — Schwegman Lundberg & Woessner, P.A.

(57) ABSTRACT

A heating assembly configured for use in mechanical testing at a scale of microns or less. The heating assembly includes a probe tip assembly configured for coupling with a transducer of the mechanical testing system. The probe tip assembly includes a probe tip heater system having a heating element, a probe tip coupled with the probe tip heater system, and a heater socket assembly. The heater socket assembly, in one example, includes a yoke and a heater interface that form a socket within the heater socket assembly. The probe tip heater system, coupled with the probe tip, is slidably received and clamped within the socket.

20 Claims, 8 Drawing Sheets

(51) Int. Cl.
*G01Q 30/02* (2010.01)
*G01Q 30/10* (2010.01)
*G01Q 60/36* (2010.01)
*G01N 3/42* (2006.01)

(52) U.S. Cl.
CPC .............. *G01Q 60/366* (2013.01); *H05B 3/03* (2013.01); *G01N 2203/0226* (2013.01); *G01N 2203/0282* (2013.01)

(56) References Cited

U.S. PATENT DOCUMENTS

| | | |
|---|---|---|
| 4,703,181 A | 10/1987 | Swann et al. |
| 4,917,462 A | 4/1990 | Lewis et al. |
| 4,992,660 A | 2/1991 | Kobayashi |
| 4,996,433 A | 2/1991 | Jones et al. |
| 5,202,542 A | 4/1993 | Ferguson |
| 5,331,134 A | 7/1994 | Kimura |
| 5,367,171 A | 11/1994 | Aoyama et al. |
| 5,512,727 A | 4/1996 | Myers et al. |
| 5,654,546 A | 8/1997 | Lindsay |
| 5,661,235 A | 8/1997 | Bonin |
| 5,731,587 A | 3/1998 | Dibattista et al. |
| 5,821,545 A | 10/1998 | Lindsay et al. |
| 5,869,751 A | 2/1999 | Bonin |
| 6,339,958 B1 | 1/2002 | Tsui et al. |
| 6,495,838 B1 | 12/2002 | Yaguchi et al. |
| 6,520,004 B1 | 2/2003 | Lin |
| 7,451,636 B2 | 11/2008 | Bradshaw et al. |
| 7,685,868 B2 | 3/2010 | Woirgard et al. |
| 8,569,714 B2 | 10/2013 | Han et al. |
| 8,631,687 B2 | 1/2014 | Patten et al. |
| 8,844,368 B2 | 9/2014 | Peecock et al. |
| 9,316,569 B2 | 4/2016 | Oh et al. |
| 2002/0110177 A1 | 8/2002 | Nakayama et al. |
| 2006/0025002 A1 | 2/2006 | Zhang et al. |
| 2006/0180577 A1 | 8/2006 | Lindeman |
| 2007/0180924 A1 | 8/2007 | Warren et al. |
| 2007/0278420 A1 | 12/2007 | Molhave |
| 2008/0092938 A1 | 4/2008 | Majumdar et al. |
| 2008/0276727 A1 | 11/2008 | Enoksson et al. |
| 2008/0290290 A1 | 11/2008 | Nagakubo et al. |
| 2009/0111701 A1 | 4/2009 | Ahn et al. |
| 2009/0120172 A1 | 5/2009 | Bradshaw et al. |
| 2009/0194689 A1 | 8/2009 | Abramson et al. |
| 2009/0206258 A1 | 8/2009 | Kasai et al. |
| 2010/0095780 A1 | 4/2010 | Oh et al. |
| 2010/0132441 A1 | 6/2010 | Oh et al. |
| 2010/0180356 A1 | 7/2010 | Bonilla et al. |
| 2010/0186520 A1 | 7/2010 | Wheeler, IV et al. |
| 2010/0212411 A1 | 8/2010 | Passilly et al. |
| 2010/0294147 A1 | 11/2010 | Loiret-bernal et al. |
| 2011/0107472 A1 | 5/2011 | Han et al. |
| 2011/0152724 A1 | 6/2011 | Hansma et al. |
| 2011/0252874 A1 | 10/2011 | Patten et al. |
| 2011/0277555 A1* | 11/2011 | Peecock et al. .............. 73/827 |
| 2012/0292528 A1 | 11/2012 | Oh et al. |
| 2014/0331782 A1 | 11/2014 | Keranen et al. |
| 2015/0033835 A1 | 2/2015 | Asif et al. |
| 2015/0179397 A1 | 6/2015 | Damiano, Jr. et al. |
| 2016/0123859 A1 | 5/2016 | Oh et al. |

FOREIGN PATENT DOCUMENTS

| | | |
|---|---|---|
| JP | 4996867 U | 8/1974 |
| JP | 55088256 A | 7/1980 |
| JP | 6327731 A | 3/1983 |
| JP | 58173159 U | 11/1983 |
| JP | 01081553 U | 5/1989 |
| JP | 2009526230 A | 7/2009 |
| JP | 2009193833 A | 8/2009 |
| JP | 2015501935 A | 1/2015 |
| WO | WO-2008061224 | 5/2008 |
| WO | WO-2011066018 A1 | 6/2011 |
| WO | WO-2011104529 A1 | 9/2011 |
| WO | WO-2013074623 A1 | 5/2013 |
| WO | WO-2013082145 A1 | 6/2013 |
| WO | WO-2013082148 A1 | 6/2013 |
| WO | WO-2013187972 A1 | 12/2013 |

OTHER PUBLICATIONS

"U.S. Appl. No. 13/510,825, Preliminary Amendment filed May 18, 2012", 3 pgs.

"U.S. Appl. No. 14/361,094, Preliminary Amendment filed May 28, 2014", 8 pgs.

"U.S. Appl. No. 14/361,133, Preliminary Amendment filed May 28, 2014", 8 pgs.

"Application Serial No. PCT/US2012/065009, Article 19 Amendment filed Mar. 25, 2013", 6 pgs.

"International Application Serial No. PCT/US2012/065009, Supplemental Article 19 Amendment filed Apr. 26, 2013", 12 pgs.

"International Application Serial No. PCT/US2012/065009, International Preliminary Report on Patentability mailed May 30, 2014", 7 pgs.

"International Application Serial No. PCT/US2012/066842, Demand and Response filed Sep. 27, 2013 to Written Opinion mailed Feb. 7, 2013", 25 pgs.

"International Application Serial No. PCT/US2012/066842, International Preliminary Report on Patentability mailed Jun. 12, 2014", 10 pgs.

"International Application Serial No. PCT/US2012/066846, Demand and Response filed Sep. 27, 2013 to Written Opinion mailed Feb. 6, 2013", 26 pgs.

"Japanese Application Serial No. 2012-541077, Office Action mailed Mar. 18, 2014", 4 pgs.

"U.S. Appl. No. 13/510,825, Examiner Interview Summary mailed Nov. 18, 2014", 3 pgs.

"U.S. Appl. No. 13/510,825, Final Office Action mailed Dec. 26, 2014", 17 pgs.

"U.S. Appl. No. 13/510,825, Response filed Mar. 25, 2015 to Final Office Action mailed Dec. 26, 2014", 22 pgs.

"U.S. Appl. No. 13/510,825, Response filed Nov. 19, 2014 to Non Final Office Action mailed Jun. 3, 2014", 20 pgs.

"European Application Serial No. 12849761.7, Office Action mailed Jun. 27, 2014", 3 pgs.

"Japanese Application Serial No. 2014-541415, Office Action mailed Dec. 2, 2014", with English translation of claims, 6 pgs.

"U.S. Appl. No. 13/090,036, Notice of Allowance mailed Mar. 19, 2013", 8 pgs.

"U.S. Appl. No. 13/090,036, Notice of Allowance mailed Jul. 15, 2013", 9 pgs.

"U.S. Appl. No. 13/510,825 , Response filed Jun. 27, 2013 to Non Final Office Action mailed Mar. 27, 2013", 30 pgs.

"U.S. Appl. No. 13/510,825, Examiner Interview Summary mailed Jul. 10, 2013", 3 pgs.

"U.S. Appl. No. 13/510,825, Final Office Action mailed Aug. 27, 2013", 26 pgs.

"U.S. Appl. No. 13/510,825, Non Final Office Action mailed Mar. 27, 2013", 14 pgs.

"U.S. Appl. No. 13/510,825, Response filed Nov. 26, 2013 to Final Office Action mailed Aug. 27, 2013", 34 pgs.

"International Application Serial No. PCT/US2010/046865, International Preliminary Report on Patentability mailed May 30, 2012", 10 pgs.

"International Application Serial No. PCT/US2010/046865, Search Report mailed Oct. 28, 2010", 2 pgs.

"International Application Serial No. PCT/US2010/046865, Written Opinion mailed Oct. 28, 2010", 8 pgs.

"International Application Serial No. PCT/US2012/065009, International Search Report mailed Jan. 25, 2013", 2 pgs.

"International Application Serial No. PCT/US2012/065009, Written Opinion mailed Jan. 25, 2013", 5 pgs.

"International Application Serial No. PCT/US2012/066842, International Preliminary Report on Patentability mailed Dec. 6, 2013", 15 pgs.

(56) References Cited

OTHER PUBLICATIONS

"International Application Serial No. PCT/US2012/066842, International Search Report mailed Feb. 7, 2013", 2 pgs.
"International Application Serial No. PCT/US2012/066842, Written Opinion mailed Feb. 7, 2013", 8 pgs.
"International Application Serial No. PCT/US2012/066846, International Preliminary Report on Patentability mailed Dec. 3, 2013", 16 pgs.
"International Application Serial No. PCT/US2012/066846, International Search Report mailed Feb. 6, 2013", 2 pgs.
"International Application Serial No. PCT/US2012/066846, Written Opinion mailed Feb. 6, 2013", 8 pgs.
"International Application Serial No. PCT/US2013/031650, International Search Report mailed May 31, 2013", 2 pgs.
"International Application Serial No. PCT/US2013/031650, Written Opinion mailed May 31, 2013", 4 pgs.
Allard, L. F., et al., "A New Paradigm for Ultra-High-Resolution Imaging at Elevated Temperatures", Microscopy and Microanalysis, 14(Supp. S2), (2008), 792-793.
Briceno, M., et al., "In-situ TEM Observations on the Sintering Process of Colloidal Gold Using an Ultra-fast Heating Stage", Microscopy and Microanalysis, 14(Suppl 2), (2008), 1336-1337.
Damiano, John, et al., "A MEMS-based Technology Platform for in-situ TEM Heating Studies", Microscopy and Microanalysis, 14(Suppl 2), (2008), 1332-1333.
Eakins, D. E., et al., "An in situ TEM study of phase formation in gold-aluminum couples", Journal of Materials Science, 39, (2004), 165-171.
Kamino, T., et al., "A newly developed high resolution hot stage and its application to materials characterization", Microsc. Microanal. Microstruct., 4, (1993), 127-135.
Kamino, T., et al., "In-situ high-resolution electron microscopy study on a surface reconstruction of Au-deposited Si at very high temperatures", Philosophical Magazine A, 75(1), (1997), 105-114.
Min, K.-H., et al., "Crystallization behaviour of ALD-Ta2O5 thin films: the application of in-situ TEM", Philosophical Magazine, 85(18), (Jun. 21, 2005), 2049-2063.
Saka, H., "In situ observation of solid-liquid interfaces by transmission electron microscopy", J. Mater. Res., 20(7), (Jul. 2005), 1629-1640.
Saka, H., "In-situ TEM observation of transformation of dislocations from shuffle to glide sets in Si under supersaturation of interstitials", Philosophical Magazine, 86(29-31), (Oct.-Nov. 2006), 4841-4850.
Tsukimoto, S., et al., "In situ high resolution electron microscopy/ electron energy loss spectroscopy observation of wetting of a Si surface by molten Al", Journal of Microscopy, 203(Pt 1), (Jul. 2001), 17-21.

Wu, Yiying, et al., "Direct Observation of Vapor—Liquid—Solid Nanowire Growth", J. Am. Chem. Soc., 123, (Mar. 13, 2001), 3165-3166.
"U.S. Appl. No. 13/510,825, Notice of Allowance mailed Aug. 28, 2015", 8 pgs.
"European Application Serial No. 12849761.7, Extended European Search Report mailed Aug. 7, 2015", 7 pgs.
"Japanese Application Serial No. 2014-541415, Response Office Action mailed Dec. 2, 2014", W/ English Claims, 6 pgs.
"U.S. Appl. No. 13/510,825, Corrected Notice of Allowance mailed Mar. 7, 2016", 2 pgs.
"U.S. Appl. No. 14/361,133, Non Final Office Action mailed Apr. 15, 2016", 10 pgs.
"European Application Serial No. 12849761.7, Response filed Feb. 29, 2016 to Extended European Search Report mailed Aug. 7, 2015", 14 pgs.
"U.S. Appl. No. 13/510,825, Notice of Allowance mailed Jan. 29, 2016", 7 pgs.
"U.S. Appl. No. 14/948,549, Preliminary Amendment filed Jan. 14, 2016", 9 pgs.
"European Application Serial No. 10833722.1, Preliminary Amendment filed Jan. 21, 2013", 21 pgs.
"European Application Serial No. 12853899.8, Extended European Search Report mailed Jun. 29, 2015", 9 pgs.
"European Application Serial No. 12853899.8, Response filed Jan. 26, 2016 to Extended European Search Report mailed Jun. 29, 2015", 12 pgs.
"European Application Serial No. 12853965.7, Extended European Search Report mailed Nov. 16, 2015", 10 pgs.
"European Application Serial No. 12853965.7, Non Final Office Action mailed Sep. 9, 2015", 5 pgs.
"Japanese Application Serial No. 2012-541077, Office Action mailed Jan. 6, 2015", W/ English Translation, 4 pgs.
"Japanese Application Serial No. 2012-541077, Response filed Apr. 2, 2015 to Office Action mailed Jan. 6, 2015", W/ English Translations, 13 pgs.
"Japanese Application Serial No. 2012-541077, Response filed Jun. 17, 2014 to Office Action mailed Mar. 18, 2014", with English translation of claims, 10 pgs.
"Japanese Application Serial No. 2014-543623. Voluntary Amendment filed Jul. 29, 2014", W/ English Claims, 18 Pgs.
"Japanese Application Serial No. 2014-543624, Voluntary Amendment filed Jul. 29, 2014", W/ English Claims, 14 pgs.
U.S. Appl. No. 13/510,825, filed Jul. 30, 2012, Micro Electro-Mechanical Heater.
U.S. Appl. No. 13/090,036, filed Apr. 19, 2011, Indenter Assembly.
U.S. Appl. No. 14/361,133, filed May 28, 2014, High Temperature Heating System.
U.S. Appl. No. 14/361,094, filed May 28, 2014, High Temperature Heating System.

* cited by examiner

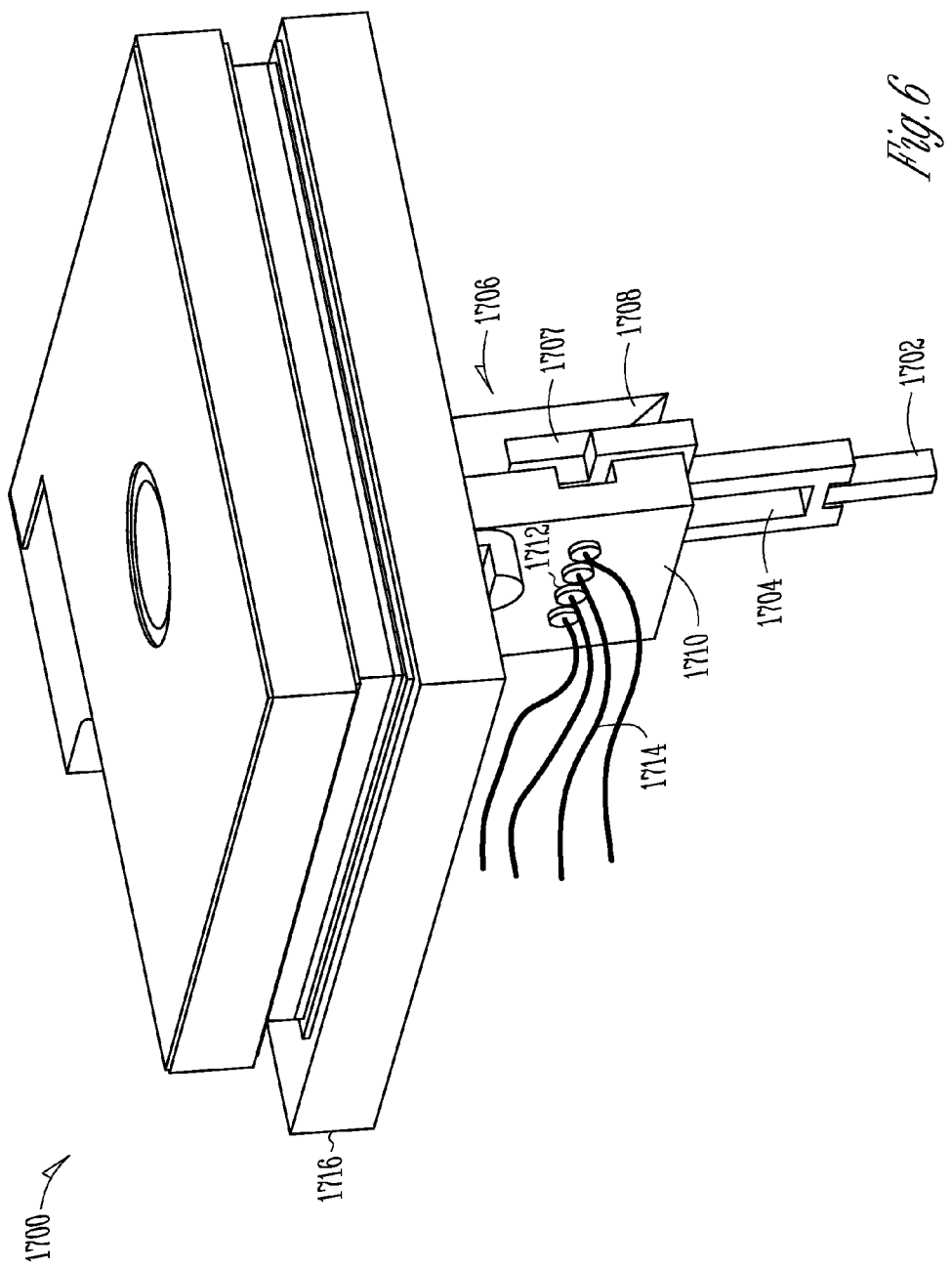

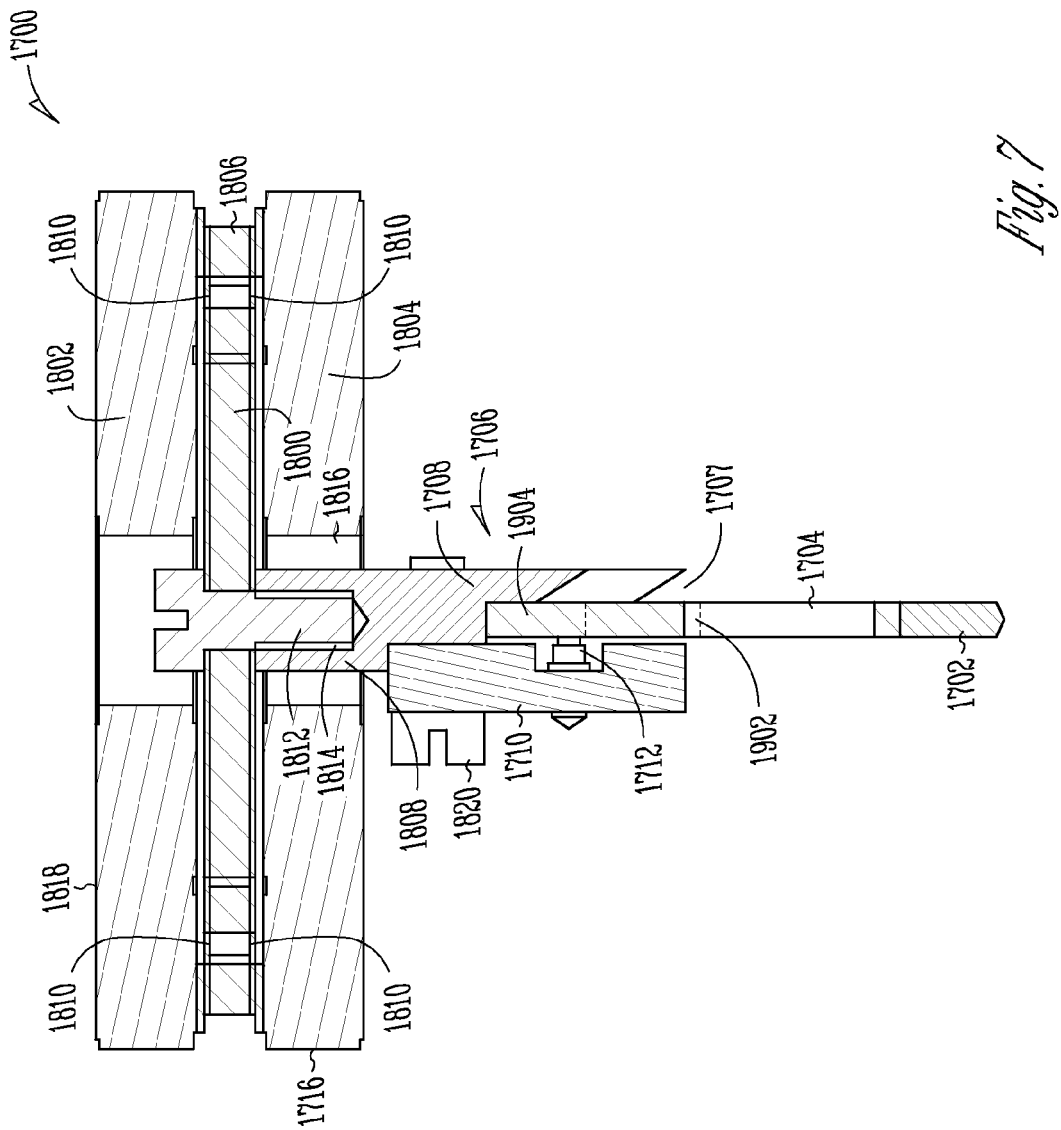

PROBE TIP HEATING ASSEMBLY

CROSS-REFERENCE TO RELATED PATENT DOCUMENTS

This application is a U.S. National Stage Application under 35 U.S.0 371 from International Application No. PCT/US2012/065009, filed on Nov. 14, 2012, published as WO 2013/074623A1, which claims the benefit of priority to U.S. Provisional Patent Application Ser. No. 61/559,699, entitled "PROBE TIP HEATING ASSEMBLY", filed on Nov. 14, 2011, all of which are hereby incorporated by reference in their entirety.

STATEMENT REGARDING FEDERALLY SPONSORED RESEARCH OR DEVELOPMENT

This invention was made with Government support under (DE-FG02-07ER84812) awarded by the Department of Energy. The Government has certain rights in this invention.

TECHNICAL FIELD

This document pertains generally, but not by way of limitation, to heated mechanical testing at scales of microns or less.

BACKGROUND

Nanoindentation is a method to quantitatively measure mechanical properties, such as elastic modulus and hardness, of materials at nanometer length scale using depth sensing indentation technique. In nanoindentation, a nanoindenter capable of determining the loading force and displacement is used Typically, a force employed in nanoindentation is less than 10 mN, with a typical displacement range being smaller than 10 µm, and with a noise level typically being better than 1 nm root mean squared (rms). The force and displacement data are used to determine a sample's mechanical properties. For sample property estimation a nanoindenter is integrated with a characterized indenter tip which has known geometry and known mechanical properties.

One of the emerging nanomechanical characterization techniques is quantitative transmission electron microscopy (TEM) in-situ mechanical testing. This testing method enables monitoring of the deformation of a sample in real time while measuring the quantitative mechanical data. Coupling a nanomechanical system with TEM imaging allows researchers to study structure property correlation and the influence of pre-existing defects on the mechanical response of materials. In addition to imaging, selected-area diffraction can be used to determine sample orientation and loading direction influence on mechanical response. Moreover, with in-situ mechanical testing, the deformation can be viewed in real-time rather than "post mortem". Performing TEM in-situ nanomechanical testing can provide unambiguous differentiation between the many possible causes of force or displacement transients which may include dislocation bursts, phase transformations, shear banding or fracture onset. Nanomechanical testing at elevated temperature is an important part of material characterization for materials having phase changes or variant mechanical properties as the temperature increases. Some of the applications of the high temperature nanomechanical test are glass transition temperature identification of polymeric and rubber materials, phase transformations of low temperature metals and shape memory alloys, study of biological samples at body temperature, simulated and accelerated thermal aging studies, accelerated material creep studies, and time-temperature-superposition curve plotting of polymers.

OVERVIEW

The present inventors have recognized, among other things, that a problem to be solved can include a fragile transducer that is subject to damage because of lateral movement and over-torquing during the installation and removal of a probe tip heater. Additionally, the electrical connections of the probe tip heater (e.g., wires and the like) must be relatively flexible to allow the transducer to freely actuate the probe and measure forces incident on the probe tip. In an example, the present subject matter can provide a solution to this problem, such as by a modular assembly including a mechanically engaging yoke that provides electrical contact features for engagement with a probe tip heater installed coincidentally with one or more transducer movement or actuator axes (e.g., without appreciable lateral forces or torque applied to the transducer during installation or removal along axes transverse to one or more transducer actuator axes). That is to say, the installation of the probe tip heater is guided along one or more desired movement axes (e.g., of a transducer) and movement of the probe tip heater during installation in one or more directions transverse to the one or more movement axes is constrained.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 6 is a perspective view of one example of a probe tip assembly.

FIG. 7 is a cross sectional view of the probe tip assembly of FIG. 6.

DETAILED DESCRIPTION

Figure 1:
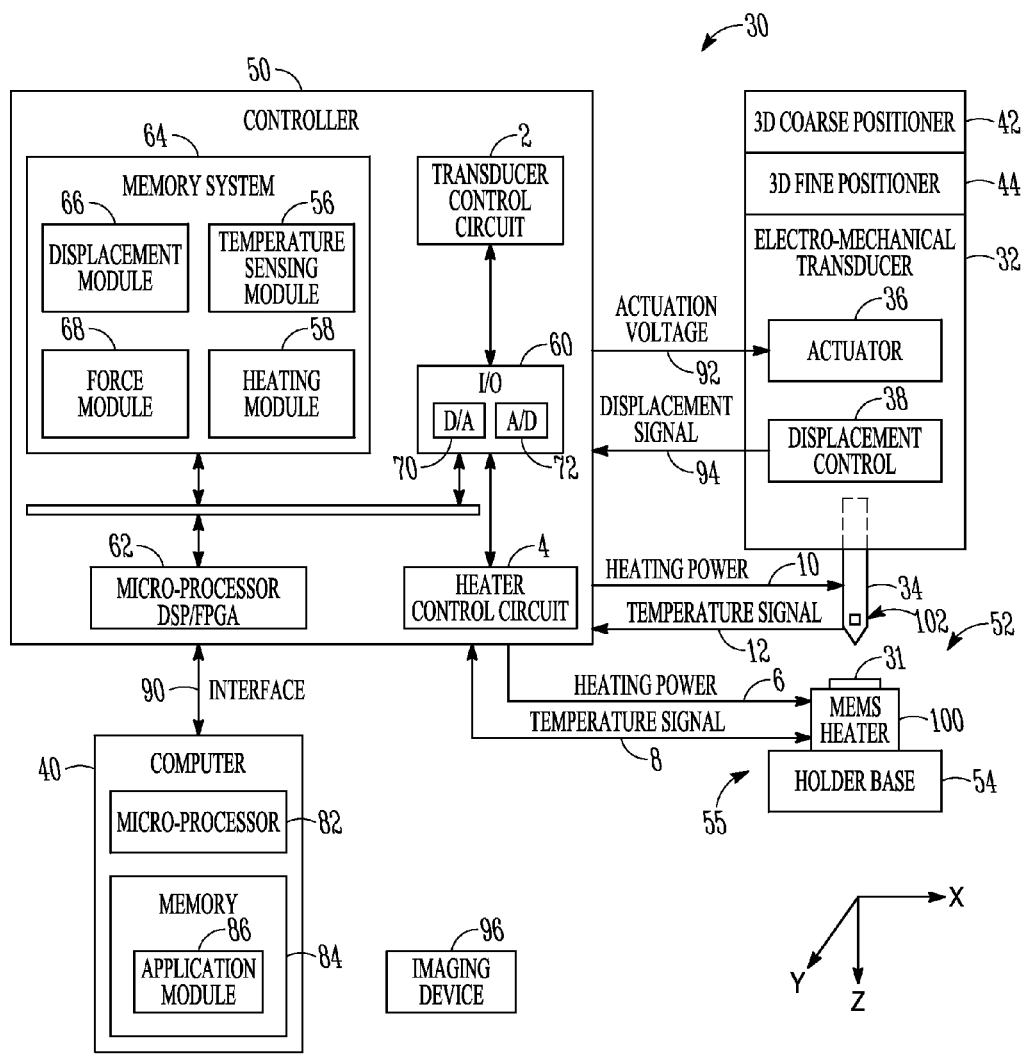
FIG. 1 is a block diagram showing one example of a nano-mechanical test system.

In the following detailed description, reference is made to the accompanying drawings which form a part hereof, and in which is shown by way of illustration how specific embodiments of the present disclosure may be practiced. In this regard, directional terminology, such as "top," "bottom," "front," "back," "leading," "trailing," etc., is used with reference to the orientation of the Figure(s) being described. Because components of embodiments of the present invention can be positioned in a number of different orientations, the directional terminology is used for purposes of illustration and is in no way limiting. These embodiments are described in sufficient detail to enable those skilled in the art to practice aspects of this disclosure, and it is to be understood that other embodiments may be utilized and that structural changes may be made without departing from the scope of the present disclosure. Therefore, the following detailed description is not to be taken in a limiting sense, and the scope of the present disclosure is defined by the appended claims and their equivalents.

According to embodiments described herein, a system and method are provided for mechanically testing small test subjects at the nano and micro scales (i.e., sub-micron scale), including, but not limited to, nanostructures, thin films and the like. Such testing is performed, in one example, to determine the mechanical properties of the materials composing the subjects. A TEM holder modification for nanomechanical testing instrumentation provides a small space constrained by the front end portion of the holder and the pole gap of a TEM electron beam. Developing a TEM in-situ nanomechanical test instrument with an integrated heater is therefore a great challenge requiring a new design and instrumentation approach. According to one embodiment, as will be described in greater detail herein, the system described herein includes a micromachined or micro-electro-mechanical (MEMS) based heater including heating and sensing elements in one or more of the sample stage or the probe assembly (e.g., at a probe tip). The heater enables the use of a nanoindenter or other instrument which provides a high precision actuation force, corresponding indenting or other deformation (e.g., indenting, scratching, pulling, compressing and the like), and high resolution displacement sensing on at least a nanometer or micrometer scale.

A probe tip assembly for use with a nanaomechanical test system (described below) is described herein. In one example, the probe tip assembly includes a probe tip and probe tip heater system configured for insertion and removal from a heater socket. The probe tip heater system and the probe tip are moved, for installation and removal, along one or more movement (actuation) axes of a test system transducer, such as capacitor with a probe shaft coupled with a center plate. Constraining movement of the probe tip and the probe tip heater system in this manner substantially prevents damage of the transducer caused with installation or removal in a direction transverse to the movement axis of the transducer. For instance, the probe tip heater system and the probe tip are installed in the heater socket without rotation or lateral movement. Instead, in an example, the components are inserted in a vertical fashion with sliding movement into the heater socket.

Additionally, the probe tip heat system described herein is configured to actively heat the probe tip, for instance to a temperature substantially matching the temperature of a sample on a sample stage. Active heating of the probe tip in this fashion substantially prevents heat transfer between the probe tip and a sample during testing and correspondingly ensures that a sample is tested at a desired temperature. Stated another way, passive heating of the probe tip through engagement with the sample (and corresponding heat transfer and temperature drop of the sample) are substantially avoided.

FIG. 1 is a schematic block diagram illustrating an example of a nanomechanical test system 30 employing a heating system 100 for heating and sensing the temperature of a small test sample 31. In addition to the heating system 100, the nanomechanical test system 30 (e.g., configured for testing at sub-micron scales) includes an electro-mechanical (EM) transducer 32 having a displaceable probe 34, an actuator 36 to displace the probe 34, a displacement sensor 38, a computer 40, a coarse positioner 42, a fine positioner 44, and a controller 50. The EM transducer 32 includes, but is not limited to, indentation, compression, tensile, fatigue, tribology, fracture instruments and the like.

The nanomechanical test system 30 further includes a test subject holder 55 including a sample stage 52 and having a base portion 54 (a holder base). The sample stage portion of the heating system 100 is positioned on the sample stage 52 (e.g., within or along the subject holder), and the holder is detachably mounted to the nanomechanical test system 30. According to one embodiment, and described in greater detail below, the heating system 100 is micromachined or MEMS based so as to fit into a small, restricted space such as for in-situ nanomechanical testing application within a quantitative transmission electron microscope (TEM), for example. As will be described below, the heating system 100 further includes in another example a probe based heater 102 configured to heat the probe 34 used for mechanical testing of a sample position on the sample stage 52.

According to one embodiment, the controller 50 includes an input/output module 60, a transducer control circuit 2, a heater control circuit 4, a processor 62, such as microprocessor or digital signal processor (DSP) and/or field programmable gate array (FPGA), for example, and a memory system 64. According to one embodiment, the memory system 64 includes a displacement module 66, a force module 68, a temperature sensing module 56, and a heating module 58. According to another embodiment, the input/output module 60 further includes a D/A converter 70, and an A/D converter 72.

In one example, the computer 40 includes a processor 82 and a memory system 84 that stores an application module 86. The computer 40 may access and communicate with the controller 50 via an interface 90 (e.g. a USB interface). FIG. 1 shows the computer 40 and controller 50 as separate entities. In other examples, the computer 40 and the controller 50 are combined as part of a single processing and control system.

According to one embodiment, the application module 86, displacement module 66, and force module 68 each include instructions respectively stored in memories 64 and 84 and which are accessible and executable by the processor 62. The memories 64 and 84 include, but are not limited to, any number of volatile or non-volatile storage devices such as RAM, flash memory, hard disk drives, CD-ROM drives, DVD drives and the like. In other embodiments, the displacement module 66, force module 68, temperature sensing module 56, and heating module 58 include any combination of hardware and software components configured to perform functions described herein. The software component of the displacement module 66 and the force module 68, the temperature sensing module 56, and the heating module 58 are each stored on a medium separate from the processing system 62 prior to being stored in memory system 64, in one example. Examples of such media include a hard disk drive, a flash memory device, a compact disc (e.g. a CD-ROM, CD-R, or CD-RW), and a digital video disc (e.g. a DVD, DVD-R, and DVD-RW), for example.

According to one embodiment, the coarse positioner 42 and the fine positioner 44 enable 3-dimensional positioning (i.e. x-, y-, and z-axes in FIG. 1) of the EM transducer 32 and displaceable probe 34 in the millimeter range with a sub-nanometer resolution. According to one embodiment, final positioning and movement of the displaceable probe 34 is performed by the actuator 36 via the application module 86 on the computer 40 and the controller 50. According to one embodiment, the controller 50 is configured to control and monitor the movement of displaceable probe 34 and to provide data representative of a displacement of the displaceable probe 34 (from the displacement sensor 38) to the computer 40 through the interface 90. According to one embodiment, the controller 50 is configured to determine and adjust a force applied to the test sample 31 by the displaceable probe 34.

According to one embodiment, the controller 50 is configured to control and monitor the temperature of the heating system 100 (including the probe based heater 102) and the test subject 31 and to provide data representative of a temperature of the heating system 100 and the test subject 31 to the computer 40 via interface 90. In one example, the controller 50 is configured to determine and adjust a heating power 6 applied to the heating system 100 and the test subject 31 to achieve a desired test subject temperature (and heater temperature) for testing and observation of the test subject. In one example, the controller 50 (e.g., the heater control circuit 4) uses the temperature signal 8 to adjust the heater power to achieve the desired test subject temperature through one or more control methods including closed loop feedback control. In a similar manner, the heater power 10 for the probe based heater 102 is adjusted by the heater control circuit 4 according to the temperature signal 12 provided from the probe based heater. Optionally, the heater control circuit 4 ensures the heating system 100 including the stage heater and the probe based heater 102 are operated cooperatively to achieve the same temperature at the displaceable probe 34 and the sample stage 52. That is to say, one or more of the heating system 100 at the sample stage 52 as well as the probe based heater 102 are actively heated to avoid passive unpredictable heating of a sample through heat transfer between the sample and the probe. Accordingly, there is minimal heat transfer through the sample 31 (e.g., between the stage 52 and the probe 34) as the heated probe 34 contacts the heated sample 31 positioned on the heated stage 52. By heating both the probe 34 and the stage 52, the heating system 100 is able to consistently and reliably test a sample 31 with the test system 30 without adversely altering the characteristics of the sample through unpredictable heat transfer caused by unheated components (e.g., the probe or the stage) in contact with the sample 31. Instead, the sample 31 temperature and the probe 34 temperature are adjusted through operated of the heating system 100 (controlled by the heater control circuit 4) to ensure the probe 34 is substantially the same temperature as the sample 31 at contact and throughout the testing procedure by way of active heating.

In operation, a user can program the controller 50 with the computer 40 through the application module 86. According to one embodiment, the controller 50, through the force module 68, provides an input or force signal 92 to the actuator 36 representative of a desired force for application to the test sample 31 by the displaceable probe 34. In response to the input actuation force signal 92, the actuator 36 drives the displaceable probe 34 toward the sample stage 52 (e.g. along the z-axis in FIG. 1). The displaceable probe 34 contacts and applies the desired force to the test subject 31. The D/A converter 70 converts the input or force signal provided by the force module 68 from digital to analog form which, in turn, is amplified to generate the actuation force 92 by transducer control circuit 2 as provided to actuator 36.

The displacement sensor 38 comprises a transducer (e.g. a capacitive transducer) which detects movement of displaceable probe 34 at least along the z-axis, and provides a displacement signal 94 to controller 50 representing measurement of the movement of the displaceable probe 34. In other embodiments, in addition to movement along the z-axis, the displacement sensor 38 detects and provides indication of other types of movement of displaceable probe 34, such as displacement along the x- and/or y-axes or rotational movement about the x- and/or y-axes. The transducer control circuit 2 conditions the displacement signal 94 from the displacement sensor 38 and sends the displacement signal 94 to the A/D converter 72. The A/D converter 72 converts the displacement signal 94 from an analog form, as received from the transducer control circuit 2, to a digital form for processing by the displacement module 66. The displacement module 66, according to one embodiment, communicates measurement of the movement of the displaceable probe 34 to the force module 68 (e.g. for force calculations) and computer 40 (via interface 90).

According to one embodiment, the controller 50 is further configured to control movement or displacement of displaceable probe 34 in the x- and y-directions relative to sample stage 52, such as by moving EM transducer 32 relative to sample stage 52 or by moving sample stage 52 relative to EM transducer 32. According to one embodiment, the nanomechanical test system 30 further includes an imaging device 96 comprising an instrument/device such as an electron microscope, an optical microscope, or a scanning probe microscope (SPM) (e.g., an atomic force microscope (AFM)) configured to provide images of a test sample 31 mounted to sample stage 52, including images of the test subject before, during and after mechanical testing such as indentation, compression, fatigue and fracture testing and the like and video of the same.

For instance, test systems suitable for configuration with the heating system 100 include, but are not limited to, optical microscopes, scanning probe microscopes (SPM), electron microscopes and the like. In each of these examples, ex-situ or in-situ heating is performed with the heating system 100 (including in one example the probe based heater 102). Another test system suitable for configuration with the heating system 100 is an electron microscopy (e.g. transmission electron (TEM) and/or scanning electron (SEM)) in-situ nanomechanical tester commercially available under the trade name PicoIndenter from Hysitron, Incorporated, of Minneapolis, Minn., USA.

During a temperature controlled mechanical testing, as will be described in greater detail below, the heating system 100 is controlled so as to heat and maintain the test subject 31 at the desired temperature. The heating system 100 is operated with at least one of open loop control or closed loop control. For more accurate temperature regulation in a changing thermal environment, the closed loop control system utilizing the temperature signal 8 as the feedback is used. When the sample 31 temperature and the probe 34 temperature reach the desired temperature, the EM transducer 32 is operated to apply a force with the moveable probe 34 to the test subject 31. According to one embodiment, the temperature of the test subject 31 is measured by the heating system 100 and the force applied and a displacement of the indented material of the test subject 31 are measured by nanomechanical test system 30. The nanomechanical test system 30 measures these parameters through the actuator 36 and the displacement sensor 38 of EM transducer 32 while optionally being synchronously imaged via the imaging device 96. The force and displacement data and images of the corresponding indentation are substantially simultaneously measured in real-time and observed by a combination of the actuator 36, the displacement sensor 38 and the imaging device 96 (e.g., an electron microscope). Stated another way, examination of the test subject—through the above described measuring and imaging techniques—at a specified testing temperature is thereby performed without any appreciable pause between measurement, imaging or heating. Phenomena including elastic or plastic deformation and the like that alter the shape of the indentation over time after application of the indentation force have minimal effect on the measurement and imaging of the indentation. Additionally, elastic or plastic deformation and the like are observable and measurable for a time period starting immediately after indentation. That is to say, because the nanomechanical test system 30 with the heating system 100 is able to perform the indentation testing, and measure and observe the material surrounding the indentation at substantially the same time, changes in the material over a period of time are similarly observable at the time of and immediately after the indentation. Observation of these parameters and phenomena at or immediately after indentation are sometimes critical in the accurate assessment and determination of corresponding material properties.

Figure 2A:
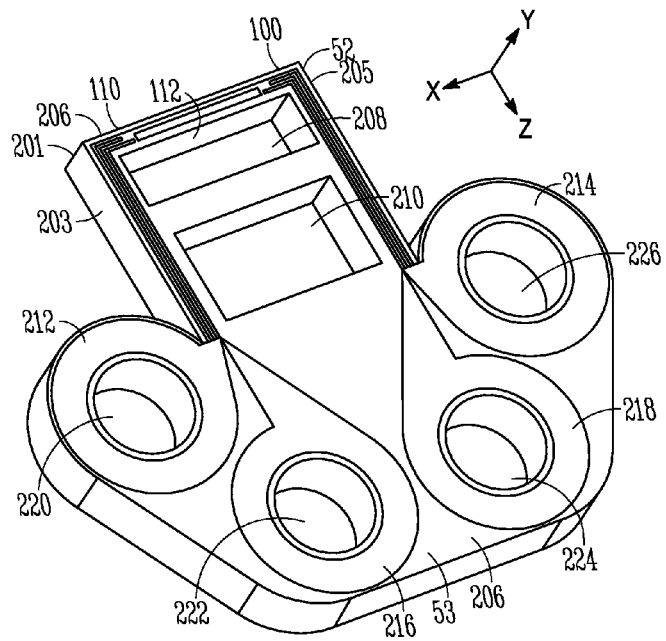
FIG. 2A is a perspective view showing one example of a sample stage and heating system.

FIGS. 2A, B show the heating system 100 designed for nanomechanical testing at a selected elevated temperature. The heating system 100, for instance, in the sample stage 52, is coupled with the base portion 54 as described above and further described below. As shown in FIG. 2A, in one example, the sample stage 52 includes a base interface 53 for coupling with the base portion 54 (i.e., the holder base, further described below) to form the test subject holder 55. The sample stage 52 further includes a test subject stage 110. For nanomechanical tests at elevated temperature, the heating system 100 mounts a test subject 31 (shown in FIG. 1) at the test subject stage 110 for interaction with the displaceable probe 34. As an example, a thin film subject is attached to the heating system 100 (e.g., the test subject stage 110) along a stage subject surface 201 and positioned perpendicular to the Z-axis for a nanoindentation experiment. For sample mounting, the stage subject surface 201 should be flat and perpendicular to the Z-axis. As described in further detail below, the stage subject surface 201 is coupled with a stage plate 112. The stage plate 112 braces the stage subject surface 201 providing mechanical stiffness and minimizes deflection of the stage subject surface during mechanical testing of a sample.

Figure 2B:
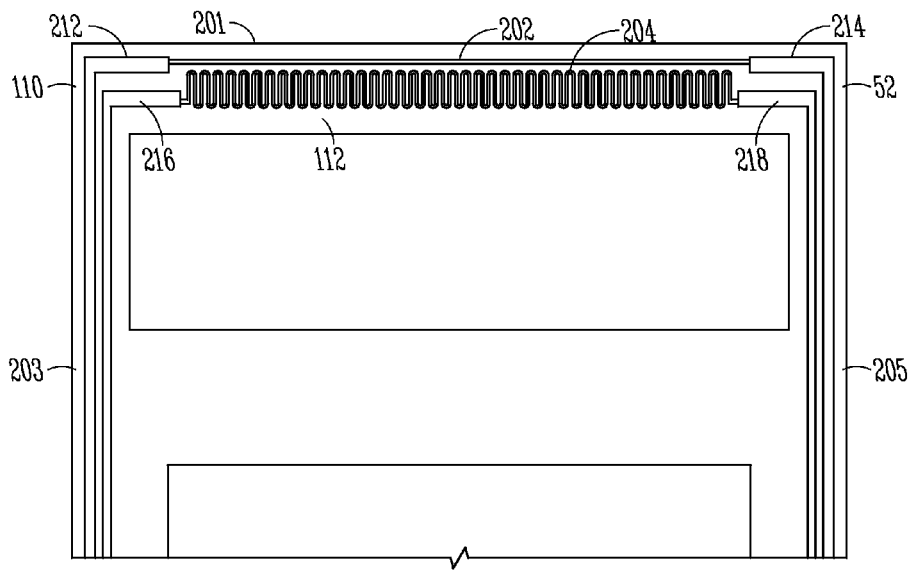
FIG. 2B is a detailed view of the heating system and sample stage shown in FIG. 2A.
Figure 3:
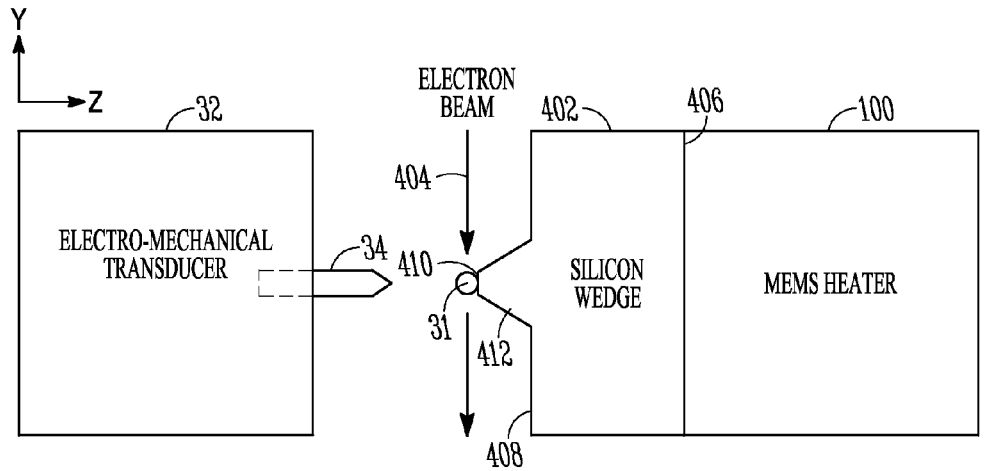
FIG. 3 is a schematic diagram of another example of a sample stage with a test sample positioned on a sample mount for mechanical testing and imaging.

The heating element 202 and the sensing element 204 are thin film resistors within a substrate 206 of the heating system 100. As shown in FIG. 2B, the heating and sensing elements 202, 204 are on the test subject stage 110 adjacent to the stage subject surface 201. Stated another way, relative to the base portion 54, 1302 (FIGS. 1 and 4) and the base interface 53, the heating element 202 and sensing element 204 are immediately adjacent to the stage subject surface 201 to ensure heat is generated and temperature is measured at a test subject and not transmitted through large portions of the sample stage 52 to a test subject 31. As described below, minimizing the distance heat is transmitted through the sample stage 52 to the test subject correspondingly minimizes mechanical drift and thermal expansion. Similarly, positioning of the heating element 202 remotely from the base portion 54, 1302 (see FIGS. 1 and 4), thermally isolates the heated test subject stage 110 from the remainder of the test subject holder 55 and further minimizes drift and expansion. Referring to FIG. 2B, positioning the heating element 202 adjacent to the stage subject surface 201 on the test subject stage 110 and away from the base interface 53 (configured for coupling to the base portion 54 shown in FIG. 1) remotely positions the heating element from the rest of the test subject holder 55.

The heating element 202 is heated by generating heating power using current flow. The sensing element 204 senses temperature in the substrate 206 by corresponding resistance variation with temperature changes. As the heating element 202 and sensing element 204 materials, metal or ceramic thin films are used. The heating element 202 and the sensing element 204 are connected to the base portion 54 of the sample stage 52 using thin-film leads 212, 214, 216 and 218. The thin film electrical leads 212, 214, 216 and 218 include one or more of metal materials, ceramic materials and the like. The electrical leads 212, 214, 216 and 218 have relatively low electrical resistance because the heating element 202 and the sensing element 204 should be the dominant resistance source. By using low electrical resistivity materials (e.g., gold), thin film leads 212, 214, 216 and 218 have correspondingly low resistance. The low resistance of the heater leads 212 and 214 prevents heat generation on the leads. Similarly, the low resistance of the sensor leads 216 and 218 prevents the addition of undesirable resistance corresponding to locations on the sample stage remote from the stage subject surface 201 and the heating element 202 for temperature measurements of the heating system 100.

The control voltage is provided by the D/A converter 70 to control the current flow though the heater control circuit 4 and the sensing element 204. The heater control circuit 4 uses either DC or AC circuitry for the resistance measurement of the sensing element 204. Since the sensing element 204 temperature change is detected by a change in resistance, for resistance detection, a Wheastone Bridge is used for the sensing circuitry in one example.

Nanomechanical testing at elevated temperature experiences thermal expansion and drift proportional to the volume and length of the materials involved (the tested sample 31 as well as the sample stage 52). Since mechanical testing relies on measured force and displacement data, thermal expansion and mechanical drift cause undesirable change in the displacement measurement data (and force calculation) and distort the mechanical properties calculated from the measured data. To minimize thermal expansion and mechanical drift, a material with low coefficient of thermal expansion and a large thermal resistance from the heating element 202 of the sample stage 52 to the base portion 54 of the test subject holder 55 are required. The heating system 100 is designed to create a large temperature drop through the heating element 202 to the base portion 54 (see FIG. 1) to minimize thermal expansion and drift within the components. To have an enhanced temperature drop from the heating element 202 to the base portion 54, the heating system 100 includes the exemplary geometry shown in FIGS. 2A, B and the materials described herein having a large thermal resistance between the heating element 202 and the base portion 54. Additionally, the materials of the sample stage 52 and at least the support columns 203, 205 have low coefficients of thermal expansion, and any thermal drift and expansion because of heating are thereby minimized within the sample stage 52.

With the large temperature drop in the heating system 100 from the heating element 202 to the base portion 54, the heated volume is limited to the portion of the heating system close to heating element 202 (e.g., the stage subject surface 201 and to a much smaller extent the support columns 203, 205 shown in FIG. 2A). The heated volume is thereby minimized and the associated thermal expansion and drift is thereby minimized throughout the test subject holder 55 including the sample stage 52 and the base portion 54 (see FIG. 1). Minimizing the heated volume of the heating system 100 also minimizes power used to heat the test sample 31 to a desired temperature since heat conduction and convection are limited to a smaller heating volume (i.e., the test subject stage 110 including the stage subject surface 201 and the stage plate 112 and to a lesser degree the support columns 203, 205 and the base interface 53). Concentrating the application of heat to the test subject stage 110 including the stage subject surface 201 also causes less thermal expansion and drift since less energy is involved in the heating process. That is to say, the geometry of the sample stage 52, the materials used therein and the location of the heating element 202 gone or together localize heating within the sample stage to the test subject stage 110. Stated another way, the materials and geometry of the sample stage 52 and the heating system 100 (e.g., the support columns 203, 205) throttle heat transfer from the sample stage 52 into larger components of the test subject holder 55 (see FIGS. 6A, B) and even the base interface 53 otherwise capable, at elevated temperatures, of greater expansion and thermal drift because of their relatively large volume and dimensions compared to the test subject stage 110 of the sample stage 52.

To increase the thermal resistance and correspondingly decrease heat transfer through the test subject holder 55, the sample stage 52 includes a material having low thermal conductivity and a minimized cross-sectional area (an area perpendicular to the z-axis and the direction of heat transfer in the example shown in FIGS. 2A, B). The thermal resistance of the material is inversely proportional to both the material thermal conductivity and the cross-sectional surface area perpendicular to a heat flux direction (e.g., the direction of heat transfer along the support columns 203, 205 from the heater 100 toward the base portion 54). The heating system 100 shown in FIG. 2 employs voids 208 and 210 with the support columns 203, 205 having minimal cross sectional area relative to the area of the test subject stage 110 to reduce the cross-sectional area perpendicular to the z-axis and enhance the thermal resistance along the z-axis. The increased thermal resistance enhances the temperature drop from the heating element 202 through the sample stage 52 when the heating system 100 is operated.

Use of low thermal conductivity material for the sample stage 52, the geometry of the stage (e.g., columns and voids), and the location of the heating element 202 adjacent to the stage subject surface 201 ensures heating of a test sample occurs at the test sample, and heat energy is minimally transmitted through the remainder of the sample stage 52 and into the test subject holder, such as the holder base 54. Because heat is generated at the test subject stage 110 adjacent to a test sample on the stage subject surface 201 heat energy must travel through the minimally thermal conductive material of the test subject stage 110 and the minimal cross sectional area of the support columns 203, 205 to reach portions of the test subject holder 55 having larger volumes and correspondingly capable of large mechanical drift and thermal expansion. Further, only minimal radiant heat from the test subject stage 110 can cross the voids 208, 210 relative to conductive heat transfer through the columns 203, 205. The voids 208, 210 thereby cooperate with the other resistive heat transfer features of the sample stage 52 to throttle heat transfer away from the test subject stage 110. These features alone or in combination thermally isolate (e.g., substantially or extensively thermally insulate) the test subject stage 110 and substantially contain heat generated therein relative to the holder base 54 and the remainder of the test subject holder 55 to minimize mechanical drift and thermal expansion through heating of the heating element 202. A minimal amount of heat is transferred to portions of the test subject holder 55 (as described below by example). In one example, the holder base 54 and the base interface 53 (FIG. 2A) are at a temperature of around 50 degrees Celsius or less (e.g., around 20 degrees Celsius) while the test subject stage 110 is heated to around 400 degrees Celsius. While complete thermal isolation is not achieved, heat transferred to the base interface 53, the holder base 54 and the remainder of the test subject holder 55 from the heated test subject stage 110 is minimal and mechanical drift and thermal expansion are correspondingly minimal Samples (e.g., sample 31) on the stage subject surface 201 are thereby held substantially static during heating, mechanical testing and observation, for instance, with a transmission electron microscope. Stated another way, observation of a micron or nanometer size discrete portion of the tested sample that is mechanically tested—as opposed to the remainder of the sample—is thereby performed prior to, during and immediately after testing because drift and expansion in components thermally isolated from the test subject stage 110 are minimized.

Since the heating system 100 is used in nanomechanical testing, the mechanical compliance of the heating system 100 is critical in one example. The enhanced stiffness (in contrast to mechanical compliance) of the sample stage 52, including the heating system 100, minimizes deflection of the sample stage and correspondingly minimizes false additional displacement measured by the probe 34 over the true actual penetration depth of the probe into the test sample 31. The stage plate 112 reinforces the stage subject surface 201 and enhances the stiffness of the sample stage 52. The material of the substrate 206 including the stage plate 112 is sufficiently stiff to not add its compliance to the mechanical data of the sample. For instance, the stage plate 112 and the substrate 206 include materials with high young's modulus, flexural modulus and the like, such as fused quartz or Zerodur. The stage plate 112 braces the stage subject surface 201 to substantially minimize deflection of the surface 201, for instance, during mechanical testing and observation. In another example, the support columns 203, 205 underlie and brace the stage subject surface 201 to enhance the stiffness of the stage subject surface. In contrast to the stiffness (the minimal mechanical compliance) of the heating system 100, other heaters use membrane structures with enhanced mechanical compliance that permit mechanical deflection of the membranes and preclude use of the heaters for accurate mechanical testing. Optionally, the stage plate 112 is an integral part of the sample stage 52. For instance, the stage plate 112 and the test subject stage 110 (including the stage subject surface 201) are formed as a single piece of the sample stage 52 with the heating system 100 disposed thereon. In another option, the stage plate 112 is coupled to the sample stage 52 to supplement the stiffness of the test subject stage 110 and the stage subject surface 201.

One of the important applications of the heating system is electron microscopy in-situ nano-mechanical testing. Since electron microscopy uses a vacuum environment, the heating system should be made of vacuum compatible materials which do not outgas in vacuum.

Fused quartz is an example of materials having low thermal expansion, low thermal conductivity, and low mechanical compliance with no out gassing in high vacuum. Fused quartz has coefficient of thermal expansion of 4.0 μm/m·K, thermal conductivity of 1.38 W/m·K, and young's modulus of 69 GPa. Those thermal and mechanical properties can provide satisfactory performance as the substrate 206 material.

The four holes 220, 222, 224 and 226 are designed for mechanical and electrical integration of the heating system 100 with the base portion 54 of the test subject holder 55. The holes 220, 222, 224 and 226 are sized and shaped for receipt of conductive fixtures (eg. conductive screws) to mechanically fix the heating system 100 to the base portion 54 of the test subject holder 55. The conductive fixtures also can make electrical connections by contacting heater and sensor leads 212, 214, 216 and 218 and the connectors on the base portion 54 of the test subject holder 55. The mechanical and electrical connections as described above are useful for TEM in-situ nanomechanical testing where minimal space is available for connection.

Since electron microscopy uses an electron beam for imaging, the test sample 31 accumulates the electrons if electrically isolated. An electron charged test sample 31 causes electrostatic force between a probe 34 and the test sample 31 and may cause a jump-to-contact as the probe 34 approaches the test sample 31. This electrostatic attraction by the accumulated electrons is undesirable for applications, such as indentation, because it distorts the measurement data, for instance the indentation loading/unloading curve. Discharging the electrons in the test sample 31 by electrically grounding the test sample improves the quantitative accuracy of mechanical measurements in electron microscopy in-situ mechanical testing.

Figure 4:
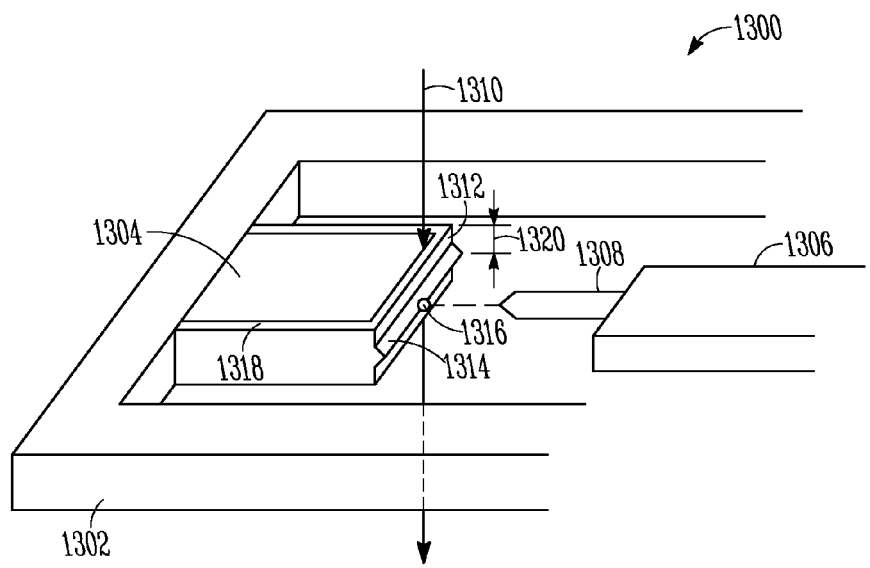
FIG. 4 is a schematic view of one example of a test subject holder with a sample stage including a heating system.

The test sample 31 is mounted directly on the stage subject surface 201 of the heating system 100, in one example. As shown in FIG. 4, for TEM in-situ nanomechanical testing, the test sample 31 is exposed to the electron beam and the beam is transmitted through the test sample 31. To make a thin test sample 31 along the electron beam 404 direction, the sample is deposited or attached on a sharp wedge-shaped sample mount 402 as shown in FIG. 4. The sample mount 402 includes a first side 408 including a sharp edge 410 along the wedge shape 412 for reception of the sample 31. A MEMS fabrication process is used to make the micro or nano scale sharp edge 410. The MEMS fabrication process includes, but is not limited to, deposition processes, focused ion beam lithography and milling, laser machining, photolithography and etching (dry or wet) and the like. With the configuration shown in FIG. 4, the test sample 31 and sample mount 402 are heated to the desired temperature using the heating system 100. After the test sample reaches the desired temperature, the EM transducer 32 (See FIG. 1) actuates the displaceable probe 34 to test the sample 31. In one example, while the probe 34 indents the test sample 31, the mechanical data and the sample image are recorded simultaneously in real time by the displacement sensor 38 and the imaging device 96, respectively. As described above, and further described herein, the probe based heater 102 elevates the temperature of the probe 34 to a temperature substantially the same as that of the test sample 31 and the underlying sample stage including the heating system 100. Accordingly, heat transfer across the sample 31 and the heated probe 34 is substantially mitigated to ensure reliable testing of the sample at the desired elevated temperature.

Because the stage subject surface 201 is parallel to the electron beam and positions the sample 31 on the sample mount 402 within the beam, electron transparency is maintained through the sample 31. Stated another way, the stage subject surface 201 and the sample mount 402 are positioned outside of the electron beam and do not underlie the beam emitter. The electron beam is thereby able to pass through the sample without distortion from underlying materials. Further, the sample stage 52 is braced by the stage plate 112 (described above and shown in FIGS. 2A, B). The stage plate 112 underlies the stage subject surface 201 and is also outside of the electron beam. Transparency of the sample 31 is thereby maintained while also providing a rigid test subject stage 110 with a stage subject surface 110. Stated another way, transmission electron microscopy is effectively performed on the sample 31 while at the same time mechanical testing (indentation, fracture, tension and the like) is permitted with negligible deformation of the underlying stage subject surface 201.

FIG. 4 shows a schematic view of one example of a test subject holder 1300. The test subject holder 1300 includes a holder base 1302 coupled with a means for holding a test subject 1304. As described herein, in some examples, the means for holding the test subject 1304 includes a test subject stage including a sample stage and a base interface (See FIGS. 2A, B). The means for holding the test subject 1304 includes a subject surface 1312 configured to position a sample 1316 within an electron beam 1310 of a transmission electron microscope. As shown in FIG. 4, the subject surface 1312 includes a surface projection 1314, for instance a wedge shaped projection, that receives a sample 1316. When installed in the transmission electron microscope, the means for holding 1304 and the subject surface 1312 positions the sample within the electron beam 1310.

The test subject holder 1300 further includes a means for heating 1318. In one example, the means for heating 1318 includes a resistive MEMS heating element on the means for holding 1304. As previously described herein, the means for heating 1318 heats a portion of the means for holding 1304 (e.g., a test subject stage 110) and the sample 1316 to a specified temperature, for instance, 400 degrees Celsius or greater. The test subject holder 1300 with the means for heating are configured for use in ex-situ and in-situ heating and observation with optical, scanning probe and electron microscopes.

Also shown in FIG. 4 is an electro-mechanical transducer 1306 with a probe 1308. The electro-mechanical transducer 1306 performs mechanical testing and measurement of the sample 1316 on the subject surface 1312. For instance, the transducer 1306 performs indentation, tensile, compression, fracture, fatigue, tribology testing and the like. Optionally, the means for heating 1318 further includes a means for heating 1319 coupled with the probe 1308. The means for heating 1319 is configured to heat the probe 1308 in a similar manner to the heating provided by the means for heating 1318 for the means for holding 1304.

As shown in FIG. 4, the means for heating 1318 is positioned adjacent to the subject surface 1312 and the sample 1316. Heating of the sample 1316 is thereby performed at the sample 1316 and not otherwise transmitted from a heating feature remote from the sample and the subject surface 1312. For instance, the means for heating 1318, such as a resistive heating element, is located adjacent to the sample 1316 according to an adjacent spacing 1320 of approximately 0.50 millimeters. As previously described in other examples and discussed again here, the means for heating 1318 is configured to heat a portion of the means for holding of the test subject 1304. For example, the means for heating 1318 is configured to heat a minimal volume of the means for holding the test subject 1304 compared to the holder base 1302 and the remainder of the means for holding coupled with the holder base. By limiting the volume heated the means for heating 1318 is able to quickly heat the portion of the means for holding with the sample 1316 thereon and use less heating energy. By maintaining the means for heating 1318 adjacent to both the sample 1316 and the subject surface 1312 rapid heating with less energy expenditure is possible because there is minimal transmission of heat energy through other portions of the means for holding the test subject 1304. As described above, positioning the means for heating 1318 according to an adjacent spacing 1320 of around 0.50 millimeters locates the heating means 1318 adjacent (e.g., immediately adjacent) to the sample 1316 and the subject surface 1312. As further discussed below, the volume heated by the means for heating 1318 is in some examples limited by features such as voids, columns and a material of the means for holding a test subject 1304. These features alone or in combination cooperate with the placement of the means for heating adjacent to the subject surface 1312 to substantially limit the volume of the means for holding 1304 heated by the means for heating 1318.

As described in other examples herein, the means for holding a test subject 1304 includes in some examples voids, supports and thermally resistive materials configured to contain heat energy within a smaller volume of the means for holding a test subject 1304 relative to the remainder of the means for holding 1304 and the holder based 1302. These features and materials are described herein and are applicable to the means for holding 1304. Referring to the sample stage 52 in FIGS. 2A and 2B, for example, the support columns 203, 205 extending from the base interface 53 to the test subject stage 110 throttle heat transfer from a first portion of the sample stage 52 (e.g., a means for holding 1304) to the base interface 53. The support columns 203, 205 have a smaller cross sectional area along a plane parallel to the plane defined by the test subject stage 110. A smaller cross sectional area in the support columns 203, 205 relative to the test subject stage 110 throttles heat transfer from the test subject stage 110 toward the base interface 53 as well as the holder base 54 shown in FIG. 1 and coupled with the base interface 53.

Additionally, one or more voids 208, 210 shown in FIGS. 2A and 2B, space the test subject stage 110 from the base interface 53 and the juncture between the base interface 53 and the holder base 54. Transmission of heat energy across the voids 208, 210 is difficult compared to conduction of heat energy through the material of the test subject holder 55. Additionally, in a vacuum (common in electron microscopes) transmission across the voids 208, 210 is only possible by minimal radiative heat transfer and not by relatively enhanced heat transfer through convection. The voids 208, 210 thereby throttle heat transfer from the test subject stage 110 to the remainder of the sample stage 52 including the base interface 53. The support columns 203, 205 (and the voids 208, 210 therebetween) position the test subject stage 110 (e.g., the subject surface 1312 including a sample 1316) remotely relative to the remainder of the sample stage 52 (means for holding a test subject 1304). The voids 208, 210 and support columns 203, 205 shown in FIGS. 2A, B thereby thermally isolate the subject surface 1312 (e.g., test subject stage) of the means for holding 1304 shown in FIG. 4 from the remainder of the means for holding and the test subject holder 1300.

While the test subject stage 110 (e.g., the subject surface 1312) is not completely thermally isolated from the remainder of the test subject holder 55 (e.g. holder 1300), heat transfer from the test subject stage 110 to the test subject holder 55 and base interface 53 is substantially minimized. For instance, in one example where a sample and the test subject stage 110 (e.g., sample 1316 and subject surface 1312) are heated to a temperature of around 400° C. or greater the remainder of the sample stage 52 adjacent to the holder base 54 is maintained at a temperature of around 50° C. or less.

Moreover, the means for holding a test subject 1304 is constructed with a thermally resistive material configured to resist conductive heat transfer from the subject surface 1312 to the holder base 1302 and a remainder of the means for holding 1304 (including for instance the base interface 53 as shown in FIG. 2A). For example, where the means for holding the test subject 1304 is constructed with fused quartz. Fused quartz has a coefficient of thermal expansion of around 4.0 μm/m·K and a thermal conductivity of around 1.38 w/m·K. With this minimal thermal conductivity the fused quartz substantially retards the transmission of heat from the subject surface 1312 to the holder base 1302. Further fused quartz experiences minimal thermal expansion at the heated subject surface 1312 because of its low coefficient of thermal expansion.

These features described immediately above and herein including the columns 203, 205, voids 208, 210 as well as the materials of the means for holding the test subject 1304 operate alone or together to thermally isolate and thereby substantially retard heat transfer from the subject surface 1312 to the remainder of the means for holding a test subject 1304 and the holder base 1302. These features either alone or in combination ensure that heating through the means for heating 1318 of the sample 1316 is substantially contained adjacent to the subject surface 1312 to provide rapid heating of the sample 1316 with relatively low amounts of heat energy. Stated another way, because of the thermal isolation of the subject surface 1312 and sample 1316, the means for heating 1318 substantially heats the subject surface 1312 and the sample 1316 while only minimally transmitting heat from the subject surface to the remainder of the means for holding 1304 (including for example, the base interface 53 and the holder base 55 shown in FIG. 1).

Because heating of the subject surface 1312 is substantially localized at the subject surface and the sample 1316 with only minimal heat transferred to the remainder of the means for holding 1304, mechanical drift and thermal expansion of the material of the means for holding the test subject 1304 as well as the holder base 1302 are substantially minimized Mechanical drift and thermal expansion of the materials comprising the holder base 1302 and the means for holding the test subject 1304 are proportional to the dimensions and volume of the materials of each of those elements heated during operation of the means for heating 1318. Because the volume heated by the means for heating 1318 is substantially limited to the subject surface 1312 and the sample 1316 mechanical drift and thermal expansion are thereby minimized. For example, with the minimal heat transfer through the support columns 203, 205 and across the voids 208, 210 along with the thermally resistive material of the means for holding, the remainder of the means for holding and the holder base 1302 experience minimal heating and thereby experience minimal mechanical drift and thermal expansion. In another example, the sample surface 1312 is constructed with a material, such as fused quartz, having a low coefficient of thermal expansion. Heating of the sample surface 1312 thereby results in minimal thermal expansion of the surface.

A portion of the sample 1316 observed, for instance, through transmission electron microscopy is thereby held substantially static during heating with the means for heating 1318. The sample 1316 including the portion observed, is further held statically for both mechanical testing with the electro-mechanical transducer 1306 and observation by the electron beam 1310 of a transmission electron microscope. That is to say, a portion of the sample 1316 at a micron or less scale (e.g., nano-scale) is observable by a transmission electron microscope during heating as well as mechanical deformation and testing and thereafter. Mechanical properties of the material making up the sample 1316 are thereby observable before heating, during heating, during mechanical testing and immediately thereafter by observation of one discrete portion of the sample throughout testing.

Additionally, as described herein, the means for holding a test subject 1304 in other examples includes a support, such as a stage plate 112 shown in FIG. 2A. The support braces the subject surface 1312 of the means for holding 1304. The support (e.g., the stage plate 112) braces the subject surface 1312 and the sample and minimizes deflection of the subject surface during mechanical testing with the electro-mechanical transducer 1306. Observation of the sample 1316 and accurate assessment of the sample properties are thereby possible through a transmission electron microscope without the distortion caused by deflection of the subject surface.

As described above, the subject surface 1312 with the support provides a robust surface for positioning and observation of the sample 1316. Because the sample 1316 is positioned on the subject surface 1312 and because the surface is positioned outside of the electron beam 1310 electron transparency is maintained through the sample 1316 thereby providing distortion free observation of the sample 1316. Stated another way, the subject surface 1312 supports the sample 1316 during mechanical testing with the electro-mechanical transducer 1306 and minimizes deflection of the surface and the sample while also maintaining electron transparency of the sample 1316. For instance, as shown in FIG. 4, the subject surface 1312 is oriented parallel to the electron beam 1310 with the surface projection 1314 presenting the sample 1316 and extending toward the electron beam 1310. Because the sample 1316 is provided along the edge of the surface projection 1314 the sample itself as opposed to the subject surface 1312 is positioned within the electron beam 1310 to maintain electron transparency.

Figure 5:
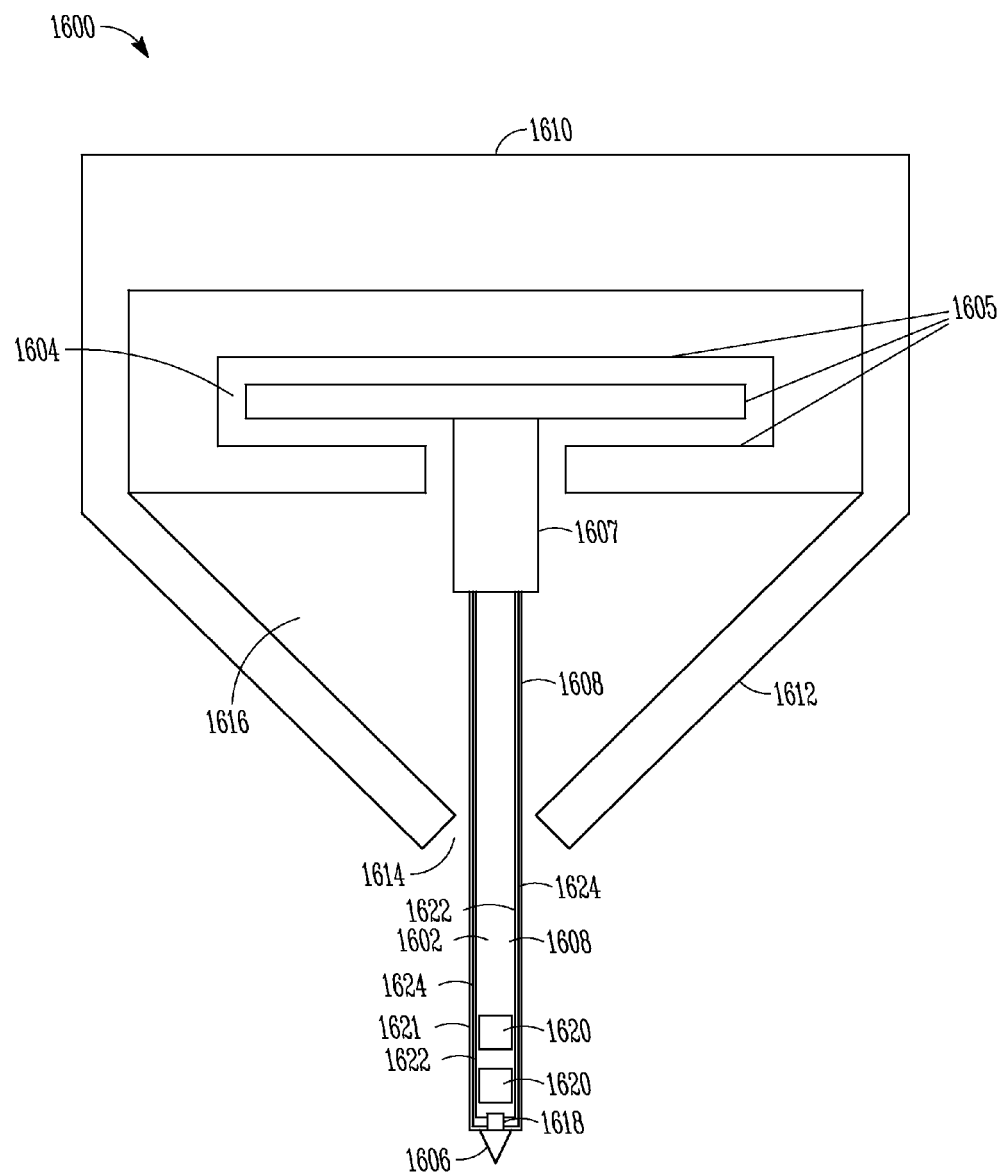
FIG. 5 is a schematic diagram showing one example of a heated mechanical testing tip assembly.

Referring now to FIG. 5, one example of an instrument assembly 1600 is shown, including a tip heater assembly 1618 (e.g., the probe based heater 102 shown in FIG. 1). The instrument assembly 1600 includes a tip assembly 1602 having the tip heater assembly 1618, a probe tip 1606, such as a diamond tip, and an extension shaft 1608. In one example, the extension shaft 1608 includes, but is not limited to, a quartz tip extension having a minimal coefficient of thermal expansion and a minimal thermal conductivity. The instrument assembly 1600 further includes a transducer assembly 1604 including two or more capacitor plates 1605 configured to measure movement of the tip assembly 1602 (e.g., the probe tip 1606) and also perform mechanical testing on a sub-micron scale (e.g., nano-scale) such as indentation, scratching and the like. In another example, the instrument assembly 1600 includes instruments to measure tension, compression, fracture testing and the like. The transducer assembly 1604 measures movement of the probe tip 1606 and also is capable of moving the probe tip 1606 for mechanical testing (such as indentation). The tip assembly 1602 is coupled with the transducer assembly 1604 by an interconnect 1607 extending therebetween. In one example, the interconnect 1607 is constructed with, but not limited to, materials including MACOR®, ZERODUR® and the like. As with the extension shaft 1608, the interconnect 1607 is constructed with materials having low coefficients thermal expansion and minimal thermal conductivities. The instrument assembly 1600 further includes a tip base 1610 (e.g., heat sink) sized and shaped to couple with an instrument including, but not limited to, scanning microscopes, electron microscopes, optical microscopes and the like.

Referring again to FIG. 5, the extension shaft 1608 is shown extending through a heat shield orifice 1614 of a heat shield 1612. As shown, the extension shaft 1608 as well as the interconnect 1607 are positioned within a heat shield cavity 1616 of the instrument assembly 1600. In one example, the heat shield 1612 is a convective heat shield including inlet and outlet ports for transmission of refrigerant fluids including chilled water, glycol, ammonia and the like. In another example, the heat shield 1612 is constructed with materials having low coefficients of thermal expansion and minimal thermal conductivities. In still another example, the heat shield 1612 is coupled with a heat sink that forms the tip base 1610. The tip base is constructed with similar materials (with low thermal conductivities and coefficients of thermal expansion) to substantially prevent heat transfer from the instrument assembly 1600 to a coupled instrument, such as a microscope. The heat shield 1612 minimizes convective and radiative heat transfer from the tip heater assembly 1618 as well as the heating system 100 as previously described herein. Throttling of heat transfer from the tip heater assembly 1618 as well as the heating system 100 into the instrument assembly 1600 including the transducer assembly 1604 substantially minimizes any thermal expansion and drift of the transducer assembly 1604 and the extension shaft 1608.

Referring again to FIG. 5 and focusing on the probe tip 1606, the tip heater assembly 1618 is shown in detail. The tip heater assembly 1618 includes a heating element and a sensor positioned immediately adjacent to the probe tip 1606. In one example, the heating element and the sensor are resistive heating and sensing elements. Positioning of the heating element and the sensor immediately adjacent to the probe tip 1606 localizes heating of the tip assembly 1602 to the volume immediately adjacent to the tip 1606. The probe tip 1606 as well as the tip heater assembly 1618 are positioned remotely from the remainder of the extension shaft 1608 by voids 1620 interposed between the tip heater assembly 1618 and the remainder of the shaft. The voids 1620, as shown in FIG. 5, are bounded by support columns 1621 extending between along the extension shaft 1608 to the tip heater assembly 1618. Sensor leads 1622 and heating element leads 1624, in one example, extend through the extension shaft 1608 including the support columns 1621 for electrical coupling with the tip heater assembly 1618.

In a similar manner to the heating system 100, the instrument assembly 1600 including the tip heater assembly 1618 (e.g., the probe based heater 102) heats the probe tip 1606 locally without undesirable significant heat transfer through the remainder of the extension shaft 1608 and transducer assembly 1604. The tip heater assembly 1618 is remotely positioned relative to the remainder of instrument assembly 1600 and is immediately adjacent to the probe tip 1606. Further, because the tip heater assembly 1618 and probe tip 1606 are isolated from the remainder of the extensions shaft 1608 by the voids 1620 and the support columns 1621 heat transfer from the tip heater assembly 1618 is substantially throttled into the remainder of the extension shaft 1608. The support columns 1621 minimize conductive heat transfer through minimal cross-sectional area into the portion of the extension shaft 1608 coupled with the interconnect 1607 and the transducer assembly 1604 (see FIG. 5). Additionally, the voids 1612 prevent any conduction of heat across the voids and substantially retard heat transfer by only allowing convective heat transfer (a minimal form of heat transfer relative to conductive heat transfer) and radiative heat transfer. In one example, where the instrument assembly 1600 is retained within a vacuum the voids 1620 substantially prevent any convective heat transfer from the tip heater assembly 1618 to the remainder of the extension shaft 1608 and only allow minimal radiative heat transfer across the voids. Additionally, because the extension shaft 1608 is constructed with materials having low coefficients of thermal expansion and minimal thermal conductivity heat transfer from the tip heater assembly 1618 to the remainder of the instrument assembly 1600 is minimized and corresponding thermal expansion and thermal drift of those components (the transducer assembly 1604 and a majority of the extension shaft 1608) are correspondingly minimized as well.

By localizing heating of the probe tip 1606 at the tip heater assembly 1618 only a small volume of the extension shaft 1608 relative to the entire extension shaft is heated with minimal heating power. Stated another way, minimal power is needed to heat the small volume of the tip heater assembly 1618, the portion of the extension shaft 1608 adjacent to the tip heater assembly 1618 and the probe tip 1606 relative to the larger volume of the remainder of the extension shaft 1608 and the instrument assembly 1600. The low volume and minimal heating power facilitate rapid thermal stabilization and minimize the thermal drift during mechanical testing and observation. Further, because the extension shaft 1608 positions the probe tip 1606 remotely relative to the transducer assembly 1604 as well as the of the instrument assembly 1600 thermal drift of the transducer assembly 1604 and the tip base 1610 is substantially minimized through use of the materials of the extension shaft, the geometry of the tip assembly 1602 as well as the heat shield 1612. Moreover, the geometry of the shaft including the support columns 1621 and the volume of the extension shaft 1608 including the tip heater assembly 1618 supports the probe tip 1606 and provides rigid support to ensure accurate transmission of forces from the transducer and measurement of movement of the probe tip 1606.

In an example where the instrument assembly 1600, including the tip heater assembly 1618 (e.g., the probe based heater 102), is incorporated into a system having a sample heating stage, such as the heating system 100 described herein, the probe tip 1606 is heated to a temperature identical (or nearly identical) to the temperature of the sample stage having the heating system and the sample thereon. Undesirable heat transfer from the heated sample to an otherwise cool tip is thereby substantially prevented. Stated another way, by substantially equalizing the temperatures of the probe tip 1606, the sample and the sample stage heat transfer between the tip 1606 and the sample is substantially prevented. Correspondingly, distortion of the sample and the measured mechanical properties of the sample are substantially prevented. In other devices, contact between an unheated tip and a heated sample transfers heat from the heated sample into the tip causing distortions (thermal expansion, drift and the like) in one or more of the sample and the tip thereby correspondingly distorting the properties and measurements collected by the tip.

In one example, the tip heater assembly 1618 is constructed with fabrication processes including a MEMS process. For instance, the instrument assembly 1600 is constructed with but not limited to, focused ion beam lithography and milling, laser machining, photo lithography and etching (dry or wet) and the like. In another example, the instrument assembly 1600 including the tip heater assembly 1618 is provided together with the heating system examples previously described herein (for instance as heating system configured to heat the stage, a sample on the stage as well as the probe tip to substantially the same temperatures). In still another example, the instrument assembly 1600 is provided separately from the heated test subject stage described herein.

FIG. 6 shows another example of a probe tip heating assembly 1700 usable as the probe based heater 102 shown in FIG. 1. In one example, the probe tip heating assembly 1700 includes some features similar to the tip heater assembly 1618, described herein. In another example, the probe tip heating assembly is constructed with, but not limited to, similar materials and methods to those materials and methods used to construct the tip heater assembly 1618.

FIG. 6 shows one example of a probe tip assembly 1700. The probe tip assembly 1700 as shown includes a probe tip 1702 and a probe tip heater system 1704 coupled between the probe tip 1702 and a transducer 1716. In one example, the probe tip includes materials suited for mechanical testing at scales of microns or less including, but not limited to, hard metals, carbon based or ceramic materials such as, diamond, carbide, sapphire, silicon, silicon dioxide, alumina, aluminum oxide, metal oxides, nitride, quartz, tungsten, steel and any of the these hard materials doped with one or more of metals, aluminum, carbon, cubic boron, boron, vanadium and the like. As will be described in further detail below, the probe tip heating assembly 1700 includes a system that allows for installation and remove of the probe tip 1702 and the probe tip heater system 1704 along a linear axis without torqueing of the transducer 1716. As will be described herein, in one example the probe tip 1702 and the probe tip heater system 1704 one or more insertion features that are received within a heater socket assembly 1706. The heater socket assembly 1706 includes a yoke 1708 and an opposing plate that clamp the probe tip 1702 and the probe tip heater system 1704 therein.

As shown in FIG. 6, the probe tip assembly 1700 includes a heater socket assembly 1706. In one example, the heater socket assembly 1706 provides a heater socket 1707 for reception of the probe tip heater system 1704 therein. In one example, the heater socket assembly 1706 includes a yoke 1708 and an opposing electrical interface plate 1710 to form a clamping or retention assembly for the probe tip heater system 1704. In one example, the electrical interface plate 1710 includes one or more displaceable pin contacts 1712, such as pogo pins and the like, sized and shaped to engage with corresponding electrical contact features on the probe tip heater system 1704. As further shown in FIG. 6, heater wires 1714 sized and shaped for coupling with control systems for the probe tip heater system 1704 (e.g., for operation of the heater system as well as monitoring of temperature) extend away from the probe tip heater system 1704 and are free to deflect during movement of the probe tip 1702 and the probe tip heater system 1704, for instance according to operation of the transducer 1716. In one example, the heater wires 1714 are each around 0.0012 inches or smaller.

As will be described in further detail below, the probe tip heater system 1704 in combination with the heater socket assembly 1706 provides a mechanism to couple the assembly of the probe tip heater system 1704 and the probe tip 1702 with the transducer 1716 while substantially minimizing or eliminating lateral movement of the transducer 1716 or torquing of the transducer 1716, for instance, through relative rotation of threaded features. Instead, the heater socket assembly 1706 receives the probe tip heater system 1704 through elevational positioning (e.g., linear positioning) of the probe tip heater system 1704 within the heater socket 1707. The opposed yoke 1708 and the electrical interface plate 1710 cooperate to mechanically engage and retain the probe tip heater system 1704 therein to accurately and reliably transmit forces between the probe tip 1702 and the transducer 1716 (e.g., through operation of the transducer 1716 or engagement of the tip 1702 with a sample and corresponding measurement of forces on the tip 1702 by the transducer 1716).

Referring now to FIG. 7, the probe tip assembly 1700 is shown again in cross-section in an installed configuration. As previously described, the probe tip assembly 1700 includes a probe tip 1702 coupled with a probe tip heater system 1704. The probe tip heater system 1704 is received within a heater socket 1707 of the heater socket assembly 1706 provided by the combination of the yoke 1708 and the electrical interface plate 1710.

As shown in FIG. 7, the transducer 1716, in one example, includes a capacitive transducer having a center plate 1800 and first and second opposed plates 1802, 1804. In one example, the center plate 1800 is positioned between the first and second opposed plates 1802, 1804 with the center plate support ring 1806. One or more springs or elastomeric elements 1810 extend between the center plate 1800 and the center plate support ring 1806 to allow for movable positioning of the center plate 1800 relative to the first and second opposed plates 1802, 1804, for instance, by electrostatic (or electromagnetic) operation of the transducer 1716.

In one example, the transducer 1716, for instance, the center plate 1800 includes a center plate coupling feature 1812 such as a threaded screw fixably positioned within the center plate 1800. The center plate coupling feature 1812 is sized and shaped for receipt within a coupling feature socket 1814 formed within a yoke coupling feature 1808 of the yoke 1708. In one example, the yoke feature 1808 includes corresponding threading, to the threading on the center plate coupling feature 1812. For instance, the yoke 1708 is positioned in a substantially permanent coupling with the center plate coupling feature 1812. That is to say, after installation of the yoke 1708, for instance, including coupling of the heater wire 1714 with other electrical interfaces on the transducer 1716 or other components within an instrument including the probe tip assembly 1700 the yoke 1708 is left in place in at least a semi-permanent fashion and is used to provide a fixture for elevational coupling with the probe tip heater system 1704 and the probe tip 1702. As further shown in FIG. 7, the transducer 1716, for instance, the transducer housing 1818 includes a probe passage 1816 extending through the transducer housing 1818 to allow movable positioning of the yoke 1708 therein. The probe passage 1816 thereby allows for ready movement of the assembly of the heater socket assembly 1706, the probe tip 1702 and the center plate 1800 relative to the first and second opposed plates 1802, 1804.

As further shown in FIG. 7, the probe tip heater system 1704 is in an installed configuration between the electrical interface plate 1710 and the yoke 1708 of the heater socket assembly 1706. For instance, substantially planar surfaces of the probe tip heater system 1704 are engaged with corresponding planar surfaces of the yoke 1708. Opposed surfaces of the probe tip heater system 1704 correspondingly engage with the displaceable pin contacts 1712 shown in FIG. 7. The engagement between the displaceable pin contacts 1712 as well as the planar surfaces of the yoke 1708 reliably engages and retains the probe tip heater system 1704 therein after installation, for instance, through elevation and positioning of the probe tip heater system 1704 within the heater socket 1707 (without substantial lateral or torquing movement of the probe tip heater system 1704 and the center plate 1800). As will be described in detail below, the yoke 1708 provides at least three points of contact with the probe tip heater system 1704 to support the heater system (in cooperation with the interface plate 1710) and maintain the system in the proper orientation at installation and throughout operation of the transducer, probe tip heater system 1704 and the probe tip 1702.

Figure 8:
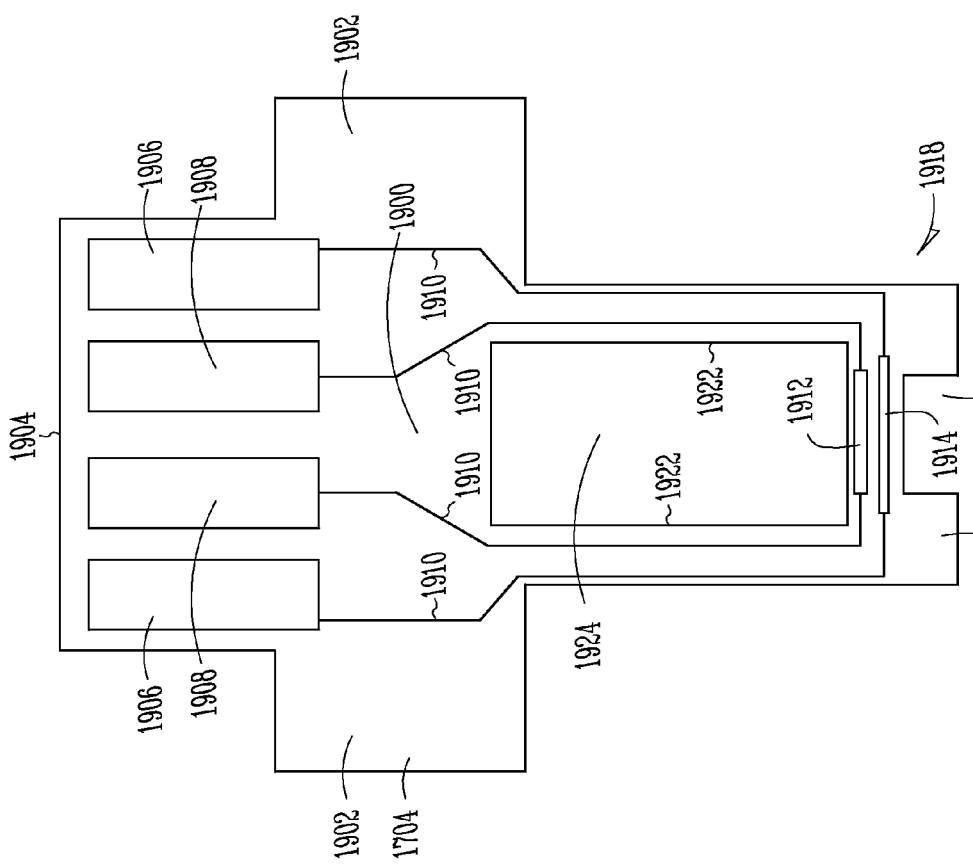
FIG. 8 is a side view of one example of the probe tip heater system.

Referring now to FIG. 8, the probe tip heater system 1704 is shown in a side view and in an uninstalled orientation relative to the probe tip assembly 1700 shown in FIG. 6. As shown, the probe tip heater system 1704 includes a heater base 1900 including one or more of heater flanges 1902 and an interface plug 1904. In the example shown in FIG. 8, the interface plug 1904 is narrower relative to the heater flanges 1902. As will be described in further detail below, the combination of the heater flanges 1902 and the interface plug 1904 cooperate with corresponding ramp surfaces of the yoke 1708 to guide and gradually engage the probe tip heater system 1704 with the displaceable pin contacts 1712. Additionally, the combination of the plurality of heater system features (flanges and plug surfaces) with the ramp surfaces of the yoke 1708 ensures the probe tip heater system 1704 is engaged on at least three points simultaneously while riding along the plurality of ramps to ensure that the probe tip heater system 1704 is reliably and accurately positioned within the heater socket assembly 1706 to provide aligned seating and retention of the probe tip heater system 1704 therein. The yoke 1708 including, for instance, the plurality of guiding ramp surfaces thereby ensures that the probe tip heater system 1704 with the probe tip 1702 coupled thereto is reliably positioned relative to the transducer 1716 to provide predictable and accurate transmission of actuation forces and measurement of forces and displacement through the probe tip heater system 1704 and the probe tip 1702. Stated another way, a heater system 1704 and probe tip 1702 are reliably coupled to the transducer 1716 through the heater socket assembly 1706 during installation (e.g., with the replacement of heater systems 1704 and probe tips 1702) in the same manner, location and orientation as a previously installed heater systems 1704 and probe tips 1702.

Referring again to FIG. 8, the interface plug of the probe tip heater system 1704, in one example, includes two or more heating element contact pads 1906 and sensing element contact pads 1908. The heating and sensing element contact pads 1906, 1908 are connected by leads 1910 with a corresponding heating element 1914 and a temperature sensing element 1912, respectively. As shown, the heating and sensing element contact pads 1906, 1908 are positioned on the interface plug 1904 to ensure reliable and consistent engagement between the contact pads and the corresponding displaceable pin contacts 1712 of the electrical interface plate 1710 (See FIG. 7).

Referring again to FIG. 8, the probe heater assembly 1918 is shown positioned remotely relative to the heater base 1900 including the heater flange 1902 and the interface plug 1904. For instance, the probe heater assembly 1918 is positioned remotely by one or more support columns 1922. As shown, the support columns 1922 have a cross-sectional area smaller than the heater flange 1902 and the assembly bridge 1920 including the heating and temperature sensing elements 1914, 1912. As shown, for instance in FIG. 8, a void 1924 is provided between the support columns 1922 and correspondingly provides a space between the heater flange 1902 and the interface plug 1904 and the probe heater assembly 1918. The support columns 1922 in combination with the void 1924, throttle heat transfer from, for instance, the probe heater assembly 1918 to the remainder of the probe tip heater system 1704. Stated another way, the heating element 1914 is configured to provide heat to the probe heater assembly 1918, for instance, at the assembly bridge 1920 including a probe tip 1702 provided therein. That is to say, the heating element 1914 heats the probe tip 1702 according to a desired set temperature provided by a user of the probe tip assembly 1700. The probe heater assembly 1918 localizes heating to the probe tip 1702 and the assembly bridge 1920. The combination of the support columns 1922 and the void 1924 substantially throttle heat transfer from the assembly bridge 1920 including, for instance, the heating element 1914 to the remainder of the probe tip heater system 1704.

In another example, and as previously described, the probe heater assembly 1918 includes a temperature sensing element 1912 adjacent to the heating element 1914. The temperature sensing element 1912, in one example, senses the temperature at the assembly bridge 1920 and thereby provides an accurate localized reading of the temperature of the probe heater assembly 1918 without skewing of temperature of the probe tip heater system 1704, for instance, at the heater flange 1902 and the interface plug 1904. Stated differently, the temperature sensing element 1912 is positioned immediately adjacent to the heating element 1914 in the probe heater assembly 1918 and is remote relative to the remainder of the probe tip heater system 1704. The temperature sensing element 1912 is thereby able to readily and accurately sense the temperature of the probe heater assembly 1918 and the probe tip 1702 without significant heat transfer from the probe heater assembly 1918 to the remainder of the probe tip heater system 1704 that would otherwise skew or lower the temperature at the probe heater assembly 1918 and the probe tip 1702. In one example, one or more of the temperature sensing element 1912 and the heating element 1914 are constructed with, but not limited to, platinum, nickel, chromium, nickel and chromium alloys, gold, copper, any electrically conductive material that can withstand the temperatures specified for the system 1704 (e.g., temperatures sufficient to heat the probe tip 1702 to 400 degrees Celsius or greater, or 600 degrees Celsius or greater).

In one example, the probe tip heater system 1704 has a substantially low coefficient of thermal expansion and low thermal conductivity. In another example, the probe tip heater system 1704 is constructed with materials having a low coefficient of thermal expansion and a low thermal conductivity, for instance materials including, but not limited to, fused quartz ZERODUR® and the like. In other examples the probe tip heater system 1704 is constructed in part or wholly from materials including, but not limited to, quartz, fused quartz, silicon dioxide, aluminum nitride, silicon carbide (doped to be electrically non-conductive) or any material or materials with low thermal expansion, low thermal conductivity and that are electrically insulating. The combination of the materials of the probe tip heater system 1704, the geometry provided by the support columns 1922, and the void 1924 remotely position the probe heater assembly 1918 relative to the remainder of the probe tip heater system 1704 and substantially constrain heat transfer from the probe heater assembly 1918 to the heater flange 1902 or the interface plug 1904. Stated another way, heat generated by the heating element 1914 is localized to the small volume of the probe heater assembly 1918 shown in FIG. 8. By heating only a small volume relative to the larger volume of the overall probe tip heater system 1704 the heating element 1914 is configured to heat the probe heater assembly 1918 including, for instance, the assembly bridge 1920 and a probe tip 1702 coupled thereto rapidly without unnecessarily heating larger volume components of the probe tip heater system 1704. Because these larger volume components, such as the heater base 1900, are not appreciably heated expansion and thermomechanical drift are substantially minimized.

Figure 9:
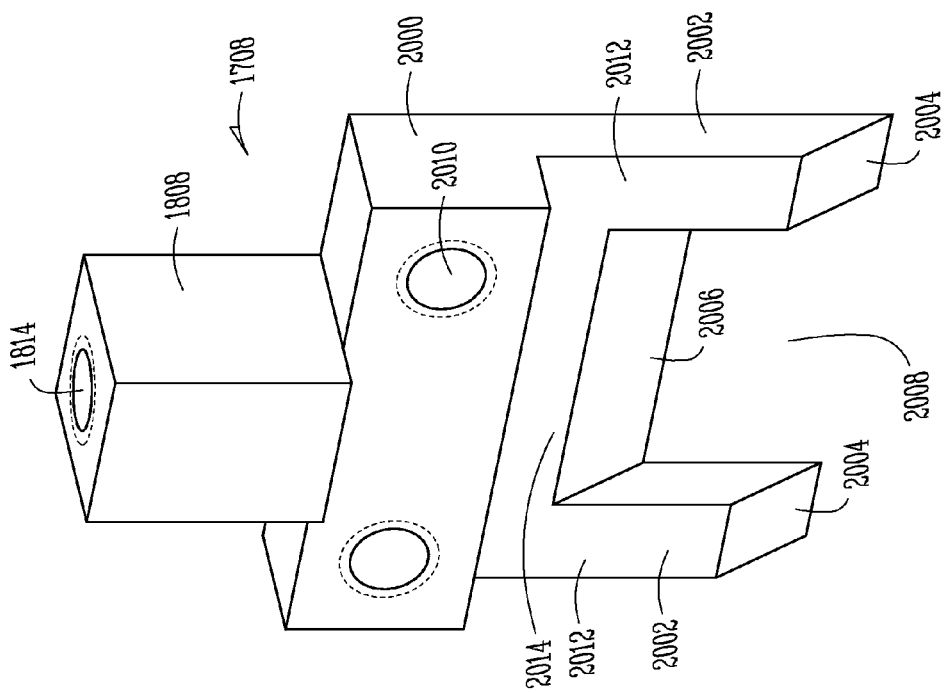
FIG. 9 is a perspective view of one example of a yoke configured to receive the probe tip heater system shown in FIG. 7.

FIG. 9 shows one example of the yoke 1708 previously shown in FIG. 6. As shown, the yoke 1708 includes a yoke base 2000 and one or more guides 2002 extending from the yoke base 2000. In one example, the one or more guides 2002 (e.g., prongs) include guide ramps 2004 providing a beveled surface at the ends of the guides 2002. In another example, the yoke base 2000 includes a plug ramp 2006 having a corresponding bevel to the guide ramps 2004. As further shown in FIG. 9, a guide recess 2008 is provided between the guides 2002 and adjacent to the plug ramp 2006. The guide ramps and the plug ramp 2004, 2006, respectively, transition from the ramp surfaces to corresponding guide planar surfaces 2012 and a base planar surface 2014. As will be described in further detail below, the probe tip heater system 1704 is configured to slidably engage the guide ramps 2004 and the plug ramp 2006 simultaneously to accurately and reliably position the probe tip heater system 1704 relative to the yoke 1708 and the electrical interface plate 1710 of the heater socket assembly 1706.

As further shown in FIG. 9, the yoke 1708 further includes, in one example, one or more interface plate sockets 2010 sized and shaped to receive one or more corresponding interface plate coupling features 1820 shown in FIG. 7. For instance, the interface plate sockets 2010 are, in one example, configured to receive pins and the like sized and shaped to couple the electrical interface plate 1710 with the yoke 1708. As further shown in FIG. 9, the coupling feature socket 1814 is sized and shaped for reception of the center plate coupling feature 1812 on the center plate 1800. In one example, the coupling feature socket 1814 is correspondingly threaded relative to threads present on a center plate coupling feature 1812, such as a threaded screw extending through the center plate 1800 as shown in FIG. 7.

In one example, the yoke 1708 is constructed with a material having a low coefficient of thermal expansion to substantially prevent expansion and corresponding measurement errors otherwise present in the system during extreme heating such as heating provided by the probe heater assembly 1918. As previously described, the probe tip heater system 1704 remotely positions the probe heater assembly 1918 relative to the remainder of the probe tip heater system. The yoke 1708 is constructed, in one example, with a material having a low coefficient of thermal expansion and low thermal conductivity to further throttle heat transfer and thereby substantially prevent or minimize the expansion of any of the components of the probe tip assembly 1700. For instance, in one example, the yoke 1708 is constructed with but not limited to materials such as INVAR®. In another example, the previously described electrical interface plate 1710 is constructed with a material such as quartz, fused quartz and the like. The electrical interface plate 1710 accordingly has a low coefficient of thermal expansion and thermal conductivity and is also electrically insulated to allow the passage of multiple displaceable pin contacts 1712 through the electrical interface plate 1710 without short circuiting between the contacts.

In operation, a previously installed assembly of the probe tip heater system 1704 and the probe tip 1702 is positioned between the electrical interface plate 1710 and the yoke 1708 on the heater socket assembly 1706. To remove the previously installed system of the probe tip 1702 and probe tip heater system 1704 (for instance, where the probe tip 1702 is worn and needs replacement) a user grasps the probe tip heater system 1704 and applies a force to the probe tip heater system along a z-axis, for instance, an axis substantially aligned with the longitudinal axis of the coupling feature socket 1814 and the center plate coupling feature 1812, as shown in FIG. 7. Stated another way, the user applies downward force to the probe tip heater system 1704 and the probe tip 1702. The downward applied force slides the probe tip heater system 1704 out from engagement between the displaceable pin contacts 1712 and the guide planar services 2012 and base planar surface 2014. Downward movement of the probe tip heater system 1704 optionally engages the transducer center plate 1800 with the second opposed plate 1804 (e.g., a supported contact that prevents further deflection of the center plate) and substantially prevents damage to the transducer. That is to say, the probe tip heater system 1704 is moved along a movement axis of the transducer for removal (and installation) to avoid movement of the transducer in a direction transversing the movement axis (e.g., the z-axis in one example).

After removal of the previously installed assembly of the probe tip heater system 1704 and the probe tip 1702 a new assembly of the probe tip heater system 1704 and a probe tip 1702 is provided. For instance, the probe tip 1702 is coupled with the probe tip heater system 1704 with a ceramic adhesive such as COTRONICS RESBOND 989FS. The assembly of the probe tip heater system 1704 and the probe tip 1702 is positioned at a preinstallation position, for instance, slightly below the heater socket 1707 (shown in FIGS. 6 and 7). The probe tip heater system 1704 is thereafter linearly elevated relative to the heater socket 1707 to position the interface plug 1904 and the heater flanges 1902 into engagement with the plug ramp 2006 and guide ramps 2004, respectively, of the guides yoke base 2000 and the guides 2002. In one example, the guide ramps 2004 and the plug ramp 2006 have identical or nearly identical bevels. The interface plug 1904 and the heater flange 1902 thereby engage each of the guide ramps and the plug ramp 2006 at a simultaneous time and are thereafter guided into the heater socket 1707 through a three point contact at spread across the guide ramps 2004 and the plug ramp 2006. The interface plug 1904 is similarly guided into the guide recess 2008 and thereafter guided up the plug ramp 2006 while the heater flanges 1902 are engaged with the guide ramps 2004. The three point contact during installation guides and supports the interface plug 1904 and the heater flange 1902 and substantially prevents misalignment during installation between the probe tip heater system 1704 and the transducer 1716.

As the probe tip heater system 1704 is further moved along the guide ramps 2004 and the plug ramp 2006 the opposed surface of the probe tip heater system 1704, for instance, shown in FIG. 7 gradually comes into contact with the displaceable pin contacts 1712. Continued upward installation of the probe tip heater system 1704 gradually biases the displaceable pin contacts 1712 and creates a firm mechanical engagement between the contacts 1712 and the yoke 1708. With continued upward installation of the probe tip heater system 1704 relative to the yoke 1708 the interface plug 1904 and the heater flange 1902 transition from the guide ramps 2004 and the plug ramp 2006 to the corresponding guide planar surfaces 2012 and the base planar surface 2014.

The guide planar surfaces 2012 and the base planar surface 2014 cooperate with the displaceable pin contacts 1712 to provide multiple planar and point contacts (e.g., at least three points of contact from the yoke 2000) on opposed sides of the probe tip heater system 1704. Through a combination of reception within the guide recess 2008, guiding by the guide ramps 2004 and the plug ramp 2006, as well as corresponding engagement with the displaceable pin contacts 1712 the probe tip heater system 1704 is successfully and reliably positioned in an installed configuration such as the configuration shown in FIG. 6. Stated another way, the probe tip heater system 1704 along with the probe tip 1702 are repeatedly capable of installation at a substantially identical position and orientation to the previously installed probe tip heater system 1704 and probe tip 1702. The consistent and predictable installation ensure reliable mechanical measurement and transmission of forces and displacements through the probe tip heater system 1704 and the probe tip 1702 relative to the transducer 1716. Further, the yoke 1708 provides at least three points of contact with the probe tip heater system 1704 through the guide surfaces 2012 and the base surface 2014 of the yoke base 2000 to support the heater system (in cooperation with the interface plate 1710) and maintain the system in the proper orientation throughout operation of the transducer, probe tip heater system 1704 and the probe tip 1702 as well as at installation.

Further, upward movement of the probe tip heater system 1704 optionally engages the transducer center plate 1800 with the first opposed plate 1802 (e.g., a supported contact that prevents further deflection of the center plate) and substantially prevents damage to the transducer 1716. Stated another way, the center plate 1800 bottoms out against the first opposed plate 1802 as it is moved upwardly during the installation procedure to arrest the center plate 1800 against further deflection. That is to say, the probe tip heater system 1704 is moved along one or more movement (actuation) axes of the transducer for removal (and installation) to avoid movement of the transducer in a direction transversing the movement axes (e.g., the z-axis in one example, and multiple axes of actuation such as x, y or z with a transducer having multiple movement or actuation axes).

Figure 10:
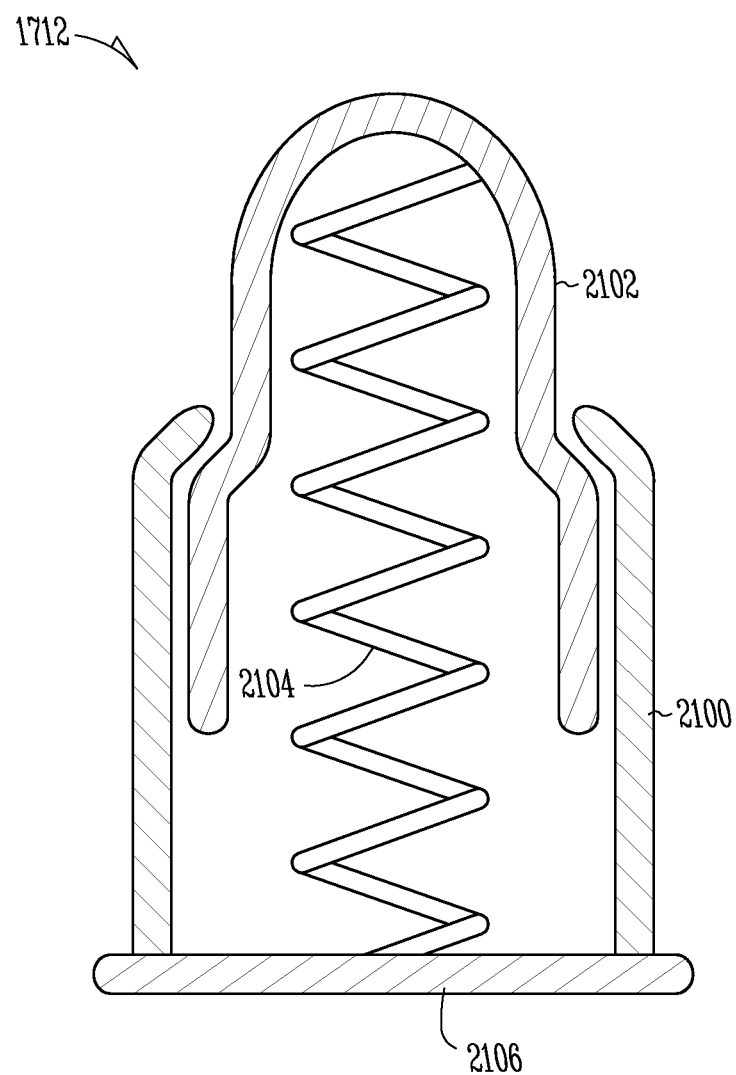
FIG. 10 is a cross sectional view of one example of a displaceable pin electrical contact.

FIG. 10 shows one example of a displaceable pin contact 1712. In one example, the displaceable pin contact 1712 includes, for instance, a pogo pin. The displaceable pin contact 1712 has a contact base 2100 and contact head 2102 movably coupled with the contact base 2100. A biasing element 2104, such as a spring, is positioned between the contact head 2102 and the contact base 2100. The biasing element 2104 biases the contact head 2102 away from the contact base 2100 and a contact interface 2106. In one example, the contact interface 2106 is sized and shaped to couple with one or more of the heater wires 1714 previously shown in FIG. 6 (e.g., by solder, mechanical joints, conductive adhesives, welding and the like). The contact head 2102 is configured for sliding engagement with the probe tip heater system 1704, for instance, along the heating element contact pads and sensing element contact pads 1906, 1908. As shown in FIG. 8, in one example, the heating element contact pads and sensing element contact pads 1908 are positioned in a similar manner to the plurality of displaceable pin contacts 1712 shown in FIG. 6. The biasing element 2104 of each of the displaceable pin contacts 1712 cooperates with the positioning of the probe tip heater system 1704 to clamp and reliably engage the probe tip heater system 1704 and the attached probe tip 1702 within the heater socket 1707 of the heater socket assembly 1706 as previously described herein.

Various Notes & Examples

Example 1 can include subject matter for a heating assembly configured for use in mechanical testing at a scale of microns or less, the heating assembly comprising: a probe tip assembly configured for coupling with a transducer of the mechanical testing system, the probe tip assembly includes: a probe tip heater system including a heater base and a heating element; a probe tip coupled with the probe tip heater system; a heater socket assembly including a yoke and a heater interface forming a socket within the heater socket assembly; and wherein the heater base is slidably received and retained within the socket.

Example 2 can include, or can optionally be combined with the subject matter of Example 1, to optionally include wherein an axis of sliding reception of the heater base with the socket is parallel to a movement axis of the transducer of the mechanical testing system.

Example 3 can include, or can optionally be combined with the subject matter of one or any combination of Examples 1 or 2 to optionally include wherein the heater base includes: one or more flanges and an interface plug; the yoke includes: one or more guides, and a yoke base; and wherein the one or more flanges and the interface plug are clamped between the heater interface and the one or more guides and the yoke base in an installed configuration.

Example 4 can include, or can optionally be combined with the subject matter of one or any combination of Examples 1 through 3 to optionally include wherein the one or more guides each include a guide ramp and guide surfaces, and the yoke base includes a plug ramp and a base surface.

Example 5 can include, or can optionally be combined with the subject matter of one or any combination of Examples 1-4 to include wherein the yoke cooperates with the probe tip heater system to guide the probe tip heater system from an intermediate installed configuration to the installed configuration: in the intermediate installed configuration the interface plug of the heater base is slidably engaged along the plug ramp of the yoke base, and the one or more flanges of the heater base are slidably engaged along the guide ramps of the one or more guides, and in the installed configuration the interface plug is engaged along the base surface of the yoke base, and the heater flanges are engaged along the guide surfaces of the one or more guides.

Example 6 can include, or can optionally be combined with the subject matter of Examples 1-5 to optionally include wherein the heater base includes an interface plug having one or more electrical contact pads in communication with the heating element, and the heater interface of the heater socket assembly is in electrical communication with the one or more electrical contact pads through reception and retaining within the socket.

Example 7 can include, or can optionally be combined with the subject matter of Examples 1-6 to optionally include wherein the heater base slidably received and retained within the socket includes the heater base clamped within the socket.

Example 8 can include, or can optionally be combined with the subject matter of Examples 1-7 to optionally include wherein the heating element of the probe tip heater system is remotely positioned relative to the heater base.

Example 9 can include, or can optionally be combined with the subject matter of Examples 1-8 to optionally include wherein an assembly bridge of the probe tip heater system includes the heating element, and the assembly bridge is spaced from the heater base with one or more support columns having a smaller cross sectional surface area than one or more of the assembly bridge and the heater base.

Example 10 can include, or can optionally be combined with the subject matter of Examples 1-9 to optionally include a test subject holder and stage heating assembly including: a holder base configured to couple with a mechanical testing instrument having a transducer configured to mechanically test a subject at a scale of microns or less, a test subject stage, the test subject stage includes a stage plate, and the test subject stage is thermally isolated from the holder base, and a stage heating element on the test subject stage and adjacent to a stage subject surface, wherein the stage heating element is configured to generate heat at the stage subject surface; wherein the transducer is coupled with the probe tip assembly including the probe tip heater system; and a controller configured to operate the stage heating element and the probe tip heater system.

Example 11 can include, or can optionally be combined with the subject matter of Examples 1-10 to optionally include wherein the heater socket assembly includes a coupling feature socket configured for coupling with a center plate coupling feature of a transducer.

Example 12 can include, or can optionally be combined with any portion or combination of any portions of any one or more of Examples 1-11 to optionally include a probe tip assembly including a heater socket assembly configured for coupling with a transducer of a mechanical testing system, the heater socket assembly including a socket; a probe tip heater system includes a heater base and a heating element, the heater base configured for reception within the socket; a probe tip coupled with the probe tip heater system, wherein the probe tip heater system and the probe tip are movable between an intermediate installed configuration and an installed configuration within the socket: in the intermediate installed configuration the heater base is slidably received along a yoke of the socket and restrained from lateral and rotational movement relative to a z-axis of the transducer, and in the installed configuration the heater base is retained between the yoke and a heater interface of the socket.

Example 13 can include, or can optionally be combined with the subject matter of Examples 1-12 to optionally include wherein in the intermediate installed configuration the heater base is slidably received along at least three separate ramp surfaces of the yoke, and the at least three separate ramp surfaces restrain the heater base from lateral and rotational movement relative to the z-axis of the transducer.

Example 14 can include, or can optionally be combined with the subject matter of Examples 1-13 to optionally include wherein wherein in the intermediate installed configuration the heater base is slidably received along at least three separate ramp surfaces of the yoke, and the at least three separate ramp surfaces guide the heater base into the installed configuration.

Example 15 can include, or can optionally be combined with the subject matter of Examples 1-14 to optionally include wherein the three separate ramp surfaces include guide ramps of two or more guides and a plug ramp of a yoke base, and the plug ramp is recessed from the guide ramps.

Example 16 can include, or can optionally be combined with the subject matter of Examples 1-15 to optionally include wherein in the installed configuration the heater base is clamped between the heater interface and at least three separate clamping surfaces of the yoke.

Example 17 can include, or can optionally be combined with the subject matter of Examples 1-16 to optionally include wherein the three separate clamping surfaces include guide surfaces of two or more guides and a base surface of a yoke base, and the base surface is recessed guide surfaces.

Example 18 can include, or can optionally be combined with the subject matter of Examples 1-17 to optionally include wherein in the intermediate installed configuration one or more displaceable contacts of the heater interface are biased toward one or more corresponding contact pads of the heater base coupled with the heating element, and in the installed configuration, the heater base is clamped between the yoke and the one or more displaceable contacts of the heater base.

Example 19 can include, or can optionally be combined with the subject matter of Examples 1-18 to optionally include wherein the heating element is spaced from the heater base by two or more support columns and a void formed by the two or more support columns, the two or more support columns having a cross sectional area smaller than a cross sectional area of an assembly bridge of the probe tip heater system having the heating element therein.

Example 20 can include, or can optionally be combined with any portion or combination of any portions of any one or more of Examples 1-19 to optionally include a method including slidably engaging a heater base of a probe tip heater system along a yoke of a heater socket assembly configured for coupling with a transducer, the yoke and a heater interface of the heater socket assembly forming a socket, wherein the probe tip heater system includes the heater base and a heating element, and a probe tip is coupled with the probe tip heater system; guiding the probe tip heater system into the socket through slidable engagement along the yoke, guiding including restraining the probe tip heater system and the probe tip from lateral and rotational movement relative to a z-axis of the transducer; and retaining the heater base between the yoke and the heater interface after the probe tip heater system is guided into the socket.

Example 21 can include, or can optionally be combined with the subject matter of Examples 1-20 to optionally include coupling the heater socket assembly with a center plate coupling feature of a transducer.

Example 22 can include, or can optionally be combined with the subject matter of Examples 1-21 to optionally include wherein slidably engaging the heater base along the yoke includes slidably engaging the heater base along at least three separate ramp surfaces of the yoke.

Example 23 can include, or can optionally be combined with the subject matter of Examples 1-22 to optionally include wherein slidably engaging the heater base along the at least three separate ramp surfaces includes slidably engaging the heater base along two or more guide ramps of two or more guides and a plug ramp of a yoke base, and the plug ramp is recessed from the two or more guide ramps.

Example 24 can include, or can optionally be combined with the subject matter of Examples 1-23 to optionally include wherein retaining the heater base includes clamping the heater base between the yoke and the heater interface.

Example 25 can include, or can optionally be combined with the subject matter of Examples 1-24 to optionally include wherein clamping the heater base includes engaging three separate clamping surfaces of the yoke with the heater base Example 26 can include, or can optionally be combined with the subject matter of Examples 1-25 to optionally include wherein slidably engaging the heater base of the probe tip heater system along the yoke includes displacing one or more displaceable contacts of the heater interface through engagement of the heater base between the yoke and the heater interface.

Example 27 can include, or can optionally be combined with the subject matter of Examples 1-26 to optionally include wherein clamping the heater base between the yoke and the heater interface includes clamping the heater between the yoke and the one or more displaceable contacts.

Example 28 can include, or can optionally be combined with the subject matter of Examples 1-27 to optionally include uninstalling the probe tip heater system from the socket of the heater socket assembly, uninstalling including sliding the heater base from between the yoke and the heater interface, the heater base restrained from lateral and rotational movement relative to the z-axis of the transducer through slidable engagement between the yoke and the heater interface.

Each of these non-limiting examples can stand on its own, or can be combined in any permutation or combination with any one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described.

However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A heating assembly configured for use in mechanical testing at a scale of microns or less, the heating assembly comprising:
    a probe tip assembly configured for coupling with a transducer of the mechanical testing system the probe tip assembly includes:
    a probe tip heater system including a heater base and a heating element,
    a probe tip coupled with the probe tip heater system,
    a heater socket assembly including a yoke and a heater interface forming a socket within the heater socket assembly, the heater interface includes one or more displaceable contacts;
    wherein the heater base is slidably received and retained within the socket, and the heater base includes
        one or more flanges and an interface plug having one or more contact pads;
    the yoke includes
        one or more guides, and
        a yoke base; and
    wherein in an intermediate installed configuration the one or more corresponding displaceable contacts of the heater interface are biased toward the one or more contact pads coupled with the heating element and the heater base is slidable toward a distal end of the socket, and in the installed configuration the heater base is clamped between the yoke and the one or more displaceable contacts of the heater base and the heater base is seated at the distal end of the socket and restrained from lateral and rotational movement relative to the transducer by at least the yoke and the heater interface.

2. The heating assembly of claim 1, wherein the one or more guides each include a guide ramp and guide surfaces, and the yoke base includes a plug ramp and a base surface.

3. The probe tip assembly of claim 2, wherein the yoke cooperates with the probe tip heater system to guide the probe tip heater system from an intermediate installed configuration to the installed configuration:
    in the intermediate installed configuration the interface plug of the heater base is slidably engaged along the plug ramp of the yoke base, and the one or more flanges of the heater base are slidably engaged along the guide ramps of the one or more guides, and
    in the installed configuration the interface plug is engaged along the base surface of the yoke base, and the heater flanges are engaged along the guide surfaces of the one or more guides.

4. A probe tip assembly configured for use in mechanical testing at a scale of microns or less, the probe tip assembly comprising:
    a heater socket assembly configured for coupling with a transducer of a mechanical testing system, the heater socket assembly including a socket;
    a probe tip heater system includes a heater base and a heating element, the heater base configured for reception within the socket;
    a probe tip coupled with the probe tip heater system, wherein the probe tip heater system and the probe tip are movable between an intermediate installed configuration and an installed configuration within the socket:
        in the intermediate installed configuration the heater base is slidably received between a yoke of the socket and a heater interface and the heater base is slidable toward a distal end of the socket, and the heater base is restrained from lateral and rotational movement relative to a z-axis of the transducer by the yoke and the heater interface,
        in the intermediate installed configuration one or more displaceable contacts of the heater interface are biased toward one or more corresponding contact pads of the heater base coupled with the heating element, and
        in the installed configuration the heater base is retained between the yoke and the one or more displaceable contacts of the heater interface of the socket and the heater base is seated at the distal end of the socket.

5. The probe tip assembly of claim 4, wherein in the intermediate installed configuration the heater base is slidably received along at least three separate ramp surfaces of the yoke, and the at least three separate ramp surfaces restrain the heater base from lateral and rotational movement relative to the z-axis of the transducer.

6. The probe tip assembly of claim 5, wherein in the intermediate installed configuration the heater base is slidably received along at least three separate ramp surfaces of the yoke, and the at least three separate ramp surfaces guide the heater base into the installed configuration.

7. The probe tip assembly of claim 5, wherein the three separate ramp surfaces include guide ramps of two or more guides and a plug ramp of a yoke base, and the plug ramp is recessed from the guide ramps.

8. The probe tip assembly of claim 4, wherein in the installed configuration the heater base is clamped between the heater interface and at least three separate clamping surfaces of the yoke.

9. The probe tip assembly of claim 8, wherein the three separate clamping surfaces include guide surfaces of two or more guides and a base surface of a yoke base, and the base surface is recessed relative to the guide surfaces.

10. The probe tip assembly of claim 4, wherein the heating element is spaced from the heater base by two or more support columns and avoid formed by the two or more support columns, the two or more support columns having a cross sectional area smaller than a cross sectional area of an assembly bridge of the probe tip heater system having the heating element therein.

11. A method of use for a probe tip assembly configured for mechanical testing at a scale of microns or less comprising:
    slidably engaging a heater base of a probe tip heater system along a yoke of a heater socket assembly configured for coupling with a transducer, the yoke and a heater interface of the heater socket assembly forming a socket, wherein the probe tip heater system includes the heater base, one or more contact pads coupled with the heater base and a heating element, and a probe tip is coupled with the probe tip heater system;
    guiding the probe tip heater system into the socket and toward a distal end of the socket through slidable engagement along the yoke in an intermediate installed configuration, guiding including restraining the probe tip heater system and the probe tip from lateral and rotational movement relative to a z-axis of the transducer with the yoke and one or more displaceable contacts of the heater interface, the one or more displaceable contacts biased toward the one or more contact pads of the heater base coupled with the heating element; and
    retaining the heater base between the yoke and the heater interface having the one or more displaceable contacts after the probe tip heater system is guided into the socket and the heater base is seated at the distal end of the socket in an installed configuration.

12. The method of claim 11 comprising coupling the heater socket assembly with a center plate coupling feature of a transducer.

13. The method of claim 11, wherein slidably engaging the heater base along the yoke includes slidably engaging the heater base along at least three separate ramp surfaces of the yoke.

14. The method of claim 13, wherein slidably engaging the heater base along the at least three separate ramp surfaces includes slidably engaging the heater base along two or more guide ramps of two or more guides and a plug ramp of a yoke base, and the plug ramp is recessed from the two or more guide ramps.

15. The method of claim 11, wherein retaining the heater base includes clamping the heater base between the yoke and the heater interface.

16. The method of claim 15, wherein clamping the heater base includes engaging three separate clamping surfaces of the yoke with the heater base.

17. The method of claim 11, wherein slidably engaging the heater base of the probe tip heater system along the yoke includes displacing the one or more displaceable contacts of the heater interface through engagement of the heater base between the yoke and the heater interface.

18. The method of claim 11 comprising uninstalling the probe tip heater system from the socket of the heater socket assembly, uninstalling including sliding the heater base from between the yoke and the heater interface, the heater base restrained from lateral and rotational movement relative to the z-axis of the transducer through slidable engagement between the yoke and the heater interface.

19. The probe tip assembly of claim 4, wherein in the intermediate installed configuration the heater base is slidable into the socket along the z-axis of the transducer.

20. The probe tip assembly of claim 1, wherein in the intermediate installed configuration the heater base is slidable into the socket along a z-axis of the transducer.

* * * * *